United States Patent
Ricci et al.

(10) Patent No.: US 10,945,845 B2
(45) Date of Patent: Mar. 16, 2021

(54) TISSUE REPAIR DEVICES AND SCAFFOLDS

(71) Applicant: New York University, New York, NY (US)

(72) Inventors: John L. Ricci, Middletown, NJ (US); Elizabeth Clark, Jersey City, NJ (US); Paulo Coelho, Brooklyn, NY (US); Elizabeth Dianne Rekow, New York, NY (US); James Smay, Stillwater, OK (US); Van P. Thompson, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/402,737

(22) PCT Filed: May 30, 2013

(86) PCT No.: PCT/US2013/043336
§ 371 (c)(1),
(2) Date: Nov. 21, 2014

(87) PCT Pub. No.: WO2013/181375
PCT Pub. Date: Dec. 5, 2013

(65) Prior Publication Data
US 2015/0150681 A1  Jun. 4, 2015

Related U.S. Application Data

(60) Provisional application No. 61/653,019, filed on May 30, 2012.

(51) Int. Cl.
*A61F 2/28* (2006.01)
*A61L 27/54* (2006.01)
(Continued)

(52) U.S. Cl.
CPC .............. *A61F 2/28* (2013.01); *A61F 2/2875* (2013.01); *A61L 27/025* (2013.01); *A61L 27/54* (2013.01);
(Continued)

(58) Field of Classification Search
CPC ..................... A61F 2/28; A61F 2/3094; A61F 2002/30011; A61F 2002/30235;
(Continued)

(56) References Cited

U.S. PATENT DOCUMENTS

| | | | | |
|---|---|---|---|---|
| 5,133,755 A | * | 7/1992 | Brekke | A61F 2/28 623/23.51 |
| 5,282,861 A | * | 2/1994 | Kaplan | A61F 2/28 427/2.26 |

(Continued)

FOREIGN PATENT DOCUMENTS

| | | |
|---|---|---|
| WO | 2002083194 | 10/2002 |
| WO | 2009021209 | 12/2009 |
| WO | 2010044758 | 4/2010 |

OTHER PUBLICATIONS

Sherwood et al., "A three-dimensional osteochondral composite scaffold for articular cartilage repair", Biomaterials, 2002, 23:4739-4751.
(Continued)

*Primary Examiner* — Alvin J Stewart
(74) *Attorney, Agent, or Firm* — Kilpatrick Townsend & Stockton LLP

(57) ABSTRACT

The present invention relates to multiphasic, three-dimensionally printed, tissue repair devices or scaffolds useful for promoting bone growth and treating bone fracture, defect or deficiency, methods for making the same and methods for promoting bone growth and treating bone fracture, defect or deficiency using the same. The scaffold has a porous bone
(Continued)

ingrowth area containing interconnected struts surrounded by a microporous shell. At the ends of the scaffold, the shell may be extended as a guide flange to stabilize the scaffold between ends of bone. The center of the scaffold may be empty and may serve as a potential marrow space. The porous ingrowth structure may be infiltrated with a soluble filler or carrier, such as, for example calcium sulfate which may be infiltrated with one or more of an antibiotic, a growth factor, a differentiation factors, a cytokine, a drug, or a combination of these agents.

26 Claims, 21 Drawing Sheets

(51) Int. Cl.
    *A61L 27/56*      (2006.01)
    *A61L 27/02*      (2006.01)
    *B33Y 80/00*      (2015.01)
    *A61F 2/30*      (2006.01)

(52) U.S. Cl.
    CPC .............. *A61L 27/56* (2013.01); *B33Y 80/00* (2014.12); *A61F 2/3094* (2013.01); *A61F 2002/2817* (2013.01); *A61F 2002/30011* (2013.01); *A61F 2002/3092* (2013.01); *A61F 2002/30235* (2013.01); *A61F 2002/30574* (2013.01); *A61F 2002/30962* (2013.01); *A61F 2002/30968* (2013.01); *A61F 2002/30985* (2013.01); *A61F 2310/00179* (2013.01); *A61L 2430/02* (2013.01)

(58) Field of Classification Search
    CPC .... A61F 2002/30574; A61F 2002/3092; A61F 2002/30962; A61F 2002/30985; A61F 2210/0076; A61F 2240/002; A61F 2240/001; A61F 2250/0023; A61F 2002/30028; A61F 2002/30971; A61F 2/30942; A61F 2002/2835; A61F 2002/2839; A61F 2/2846; B33Y 80/00
    USPC ........... 623/23.51, 23.55, 23.76, 23.6, 23.61, 623/23.72, 23.5, 23.63, 14.12
    See application file for complete search history.

(56) References Cited

U.S. PATENT DOCUMENTS

| | | | |
|---|---|---|---|
| 5,755,792 A * | 5/1998 | Brekke | A61F 2/28 128/898 |
| 5,904,717 A * | 5/1999 | Brekke | A61F 2/28 424/423 |
| 6,005,161 A * | 12/1999 | Brekke | A61F 2/28 424/422 |
| 6,013,853 A * | 1/2000 | Athanasiou | A61F 2/0811 424/423 |
| 6,027,744 A * | 2/2000 | Vacanti | A61F 2/28 424/426 |
| 6,187,329 B1 * | 2/2001 | Agrawal | A61F 2/28 424/424 |
| 6,262,332 B1 * | 7/2001 | Ketharanathan | A61L 27/48 606/151 |
| 6,264,702 B1 * | 7/2001 | Ory | D04B 21/10 602/49 |
| 6,283,997 B1 * | 9/2001 | Garg | A61F 2/28 623/16.11 |
| 6,387,693 B2 * | 5/2002 | Rieser | A61L 27/3612 435/1.1 |
| 6,419,491 B1 | 7/2002 | Ricci et al. | |
| 6,454,811 B1 * | 9/2002 | Sherwood | A61F 2/28 623/23.72 |
| 6,520,997 B1 * | 2/2003 | Pekkarinen | A61F 2/00 623/23.72 |
| 6,602,294 B1 * | 8/2003 | Sittinger | A61F 2/30756 623/23.61 |
| 6,974,625 B2 * | 12/2005 | Hunter | A61F 2/28 428/304.4 |
| 6,977,095 B1 * | 12/2005 | Marx | A61L 27/306 427/2.1 |
| 7,189,263 B2 * | 3/2007 | Erbe | A61B 17/80 424/422 |
| 7,427,293 B2 * | 9/2008 | Nycz | A61B 17/1604 606/151 |
| 7,572,291 B2 * | 8/2009 | Gil | A61F 2/30756 623/14.12 |
| 7,611,653 B1 * | 11/2009 | Elsner | B29C 70/48 264/255 |
| 7,655,047 B2 * | 2/2010 | Swords | A61B 17/8085 623/17.18 |
| 7,758,643 B2 * | 7/2010 | Stone | A61F 2/28 623/14.12 |
| 7,828,852 B2 * | 11/2010 | Bonutti | A61B 17/025 623/14.12 |
| 7,879,093 B2 * | 2/2011 | Wei | A61L 27/46 424/422 |
| 8,287,915 B2 * | 10/2012 | Clineff | A61B 17/80 424/602 |
| 8,338,498 B2 * | 12/2012 | Deslauriers | C08G 18/10 424/423 |
| 8,556,972 B2 * | 10/2013 | Gordon | A61F 2/28 623/16.11 |
| 8,702,808 B2 * | 4/2014 | Teoh | 623/23.61 |
| 8,916,228 B2 * | 12/2014 | Oh | A61L 27/56 427/2.24 |
| 9,180,010 B2 * | 11/2015 | Dong | A61F 2/28 |
| 9,205,176 B2 * | 12/2015 | Hunter | C22C 1/08 |
| 2001/0039454 A1 * | 11/2001 | Ricci | A61B 17/68 623/23.5 |
| 2002/0090725 A1 * | 7/2002 | Simpson | A61L 15/32 435/402 |
| 2002/0095219 A1 * | 7/2002 | Nelles | C12N 5/0068 623/23.72 |
| 2002/0120348 A1 * | 8/2002 | Melican | A61F 2/0045 623/23.72 |
| 2002/0143403 A1 * | 10/2002 | Vaidyanathan | A61L 27/446 623/23.51 |
| 2002/0169066 A1 * | 11/2002 | Cassidy | A61F 2/28 501/80 |
| 2002/0171178 A1 * | 11/2002 | Dean | A61F 2/28 264/401 |
| 2003/0006534 A1 | 1/2003 | Taboas et al. | |
| 2003/0021827 A1 * | 1/2003 | Malaviya | A61L 27/18 424/424 |
| 2003/0023316 A1 * | 1/2003 | Brown | A61F 2/0063 623/23.72 |
| 2003/0036800 A1 * | 2/2003 | Meredith | A61B 17/866 623/23.63 |
| 2003/0220696 A1 * | 11/2003 | Levine | A61L 27/045 623/17.17 |
| 2003/0225355 A1 * | 12/2003 | Butler | A61F 2/0063 602/48 |
| 2004/0019389 A1 * | 1/2004 | Swords | A61F 2/0059 623/23.72 |
| 2004/0133275 A1 * | 7/2004 | Mansmann | A61F 2/30756 623/14.12 |
| 2004/0199250 A1 * | 10/2004 | Fell | A61F 2/30767 623/14.12 |
| 2004/0230303 A1 * | 11/2004 | Gomes | A61F 2/28 623/16.11 |
| 2004/0241436 A1 * | 12/2004 | Hsieh | D01D 5/0007 428/361 |
| 2005/0015154 A1 * | 1/2005 | Lindsey | A61B 17/68 623/23.46 |
| 2005/0169893 A1 * | 8/2005 | Koblish | A61B 17/80 424/93.7 |
| 2005/0251268 A1 * | 11/2005 | Truncale | A61F 2/28 623/23.63 |

(56) References Cited

U.S. PATENT DOCUMENTS

| | | | |
|---|---|---|---|
| 2006/0195179 A1* | 8/2006 | Sun | A61L 27/38 623/1.54 |
| 2006/0241756 A1* | 10/2006 | Fritz | C12N 5/0655 623/14.12 |
| 2006/0247790 A1* | 11/2006 | McKay | A61F 2/28 623/23.44 |
| 2006/0292350 A1* | 12/2006 | Kawamura | A61L 27/12 428/189 |
| 2007/0083268 A1* | 4/2007 | Teoh | A61F 2/2875 623/17.19 |
| 2007/0112434 A1* | 5/2007 | Hakamatsuka | A61F 2/28 623/23.5 |
| 2007/0116734 A1* | 5/2007 | Akash | A61F 2/30 424/423 |
| 2007/0150064 A1* | 6/2007 | Ruberte | A61F 2/442 623/17.16 |
| 2007/0203584 A1* | 8/2007 | Bandyopadhyay | A61F 2/28 623/23.5 |
| 2007/0233264 A1* | 10/2007 | Nycz | A61B 17/1604 623/18.11 |
| 2007/0233275 A1* | 10/2007 | Shirahama | A61L 27/18 623/23.72 |
| 2007/0276506 A1* | 11/2007 | Troxel | A61F 2/28 623/23.63 |
| 2007/0299541 A1* | 12/2007 | Chernomorsky | A61K 49/04 623/23.72 |
| 2008/0008737 A1* | 1/2008 | Harlow | A61K 9/0024 424/423 |
| 2008/0039954 A1* | 2/2008 | Long | A61F 2/30756 623/23.76 |
| 2008/0058955 A1* | 3/2008 | Shirley | A61L 27/34 623/23.72 |
| 2008/0097605 A1* | 4/2008 | Pastorello | A61F 2/30965 623/14.12 |
| 2008/0103227 A1* | 5/2008 | Yun | B29C 67/0055 523/105 |
| 2008/0183300 A1* | 7/2008 | Seedhom | A61B 17/1659 623/23.76 |
| 2008/0188945 A1* | 8/2008 | Boyce | A61B 17/0401 623/23.61 |
| 2008/0206297 A1 | 8/2008 | Roeder et al. | |
| 2008/0208351 A1* | 8/2008 | Besenbacher | G01N 33/543 623/23.5 |
| 2008/0208358 A1* | 8/2008 | Bellamkonda | A61L 27/16 623/23.72 |
| 2008/0249632 A1* | 10/2008 | Stone | A61F 2/28 623/23.5 |
| 2008/0269895 A1* | 10/2008 | Steinwachs | A61L 27/3612 623/14.12 |
| 2009/0043398 A1* | 2/2009 | Yakimicki | B29C 41/06 623/23.51 |
| 2009/0062821 A1* | 3/2009 | Johnson | A61F 2/30756 606/151 |
| 2009/0123510 A1 | 5/2009 | Cronstein et al. | |
| 2009/0132047 A1* | 5/2009 | Mansmann | A61F 2/0811 623/14.12 |
| 2009/0157182 A1* | 6/2009 | Koblish | A61B 17/80 623/16.11 |
| 2009/0317447 A1* | 12/2009 | Hsiao | A61F 2/28 424/426 |
| 2010/0009103 A1* | 1/2010 | Kuboki | A61F 2/28 428/34.6 |
| 2010/0049322 A1* | 2/2010 | McKay | A61F 2/30756 623/16.11 |
| 2010/0075419 A1* | 3/2010 | Inagaki | A61L 27/56 435/402 |
| 2010/0136086 A1* | 6/2010 | Day | A61L 27/58 424/426 |
| 2010/0137990 A1* | 6/2010 | Apatsidis | A61L 27/56 623/17.16 |
| 2010/0161073 A1* | 6/2010 | Thomas | A61F 2/30756 623/23.5 |
| 2010/0179667 A1 | 7/2010 | Day | |
| 2010/0247598 A1* | 9/2010 | Shetty | A61L 15/26 424/423 |
| 2010/0256758 A1* | 10/2010 | Gordon | A61F 2/30756 623/16.11 |
| 2010/0268337 A1* | 10/2010 | Gordon | A61F 2/30756 623/16.11 |
| 2010/0286795 A1* | 11/2010 | Stone | A61F 2/28 623/23.72 |
| 2010/0310623 A1* | 12/2010 | Laurencin | A61F 2/28 424/423 |
| 2011/0022181 A1* | 1/2011 | Kasahara | A61L 27/14 623/23.5 |
| 2011/0046732 A1* | 2/2011 | Dyke | A61K 35/22 623/13.11 |
| 2011/0052660 A1 | 3/2011 | Yang et al. | |
| 2011/0060420 A1* | 3/2011 | Bartee | A61F 2/0063 623/23.72 |
| 2011/0066242 A1* | 3/2011 | Lu | A61K 38/18 623/13.14 |
| 2011/0093073 A1* | 4/2011 | Gatt | A61F 2/30756 623/14.12 |
| 2011/0144763 A1* | 6/2011 | Bagga | A61L 27/427 623/23.61 |
| 2011/0144764 A1* | 6/2011 | Bagga | A61F 2/28 623/23.61 |
| 2011/0158963 A1* | 6/2011 | Font Perez | A61L 27/12 424/93.7 |
| 2011/0184530 A1* | 7/2011 | Datta | A61L 27/48 623/23.72 |
| 2011/0206768 A1* | 8/2011 | Laird | A61L 27/3608 424/484 |
| 2011/0238178 A1* | 9/2011 | Downes | A61L 27/18 623/13.11 |
| 2011/0282451 A1* | 11/2011 | Sporring | A61F 2/30907 623/14.12 |
| 2011/0307073 A1* | 12/2011 | Teoh | A61F 2/28 623/23.61 |
| 2011/0313538 A1* | 12/2011 | Oh | A61L 27/56 623/23.61 |
| 2012/0010728 A1* | 1/2012 | Sun | A61L 27/50 623/23.72 |
| 2012/0150299 A1* | 6/2012 | Ergun | B29C 47/6037 623/17.11 |
| 2012/0165939 A1* | 6/2012 | Kladakis | A61F 2/30756 623/14.12 |
| 2012/0177939 A1* | 7/2012 | Longepied | A61F 2/28 428/546 |
| 2012/0245703 A1* | 9/2012 | Meredith | A61F 2/28 623/23.51 |
| 2012/0245706 A1* | 9/2012 | Alavi | A61L 27/446 623/23.72 |
| 2012/0265321 A1* | 10/2012 | Miller | A61F 2/28 623/23.51 |
| 2012/0271418 A1* | 10/2012 | Hollister | A61F 2/28 623/17.11 |
| 2013/0123935 A1* | 5/2013 | Hunt | A61F 2/28 623/23.61 |
| 2013/0123939 A1* | 5/2013 | Nauman | A61F 2/02 623/23.72 |
| 2013/0158672 A1* | 6/2013 | Hunt | A61F 2/30767 623/23.5 |
| 2013/0172999 A1* | 7/2013 | Kaplan | A61L 27/3604 623/14.12 |
| 2013/0178947 A1* | 7/2013 | Monaghan | A61L 27/56 623/23.55 |
| 2013/0183352 A1* | 7/2013 | Xie | A61L 27/3834 424/400 |
| 2013/0211536 A1* | 8/2013 | Metzger | A61F 2/28 623/23.5 |
| 2013/0226313 A1* | 8/2013 | Aiazian | A61L 31/129 623/23.72 |
| 2013/0268085 A1* | 10/2013 | Dong | A61F 2/28 623/23.5 |
| 2013/0325142 A1* | 12/2013 | Hunter | C22C 1/08 623/23.51 |

(56) References Cited

U.S. PATENT DOCUMENTS

| | | | |
|---|---|---|---|
| 2014/0025179 A1* | 1/2014 | Fortini | A61F 2/28 623/23.5 |
| 2014/0188242 A1* | 7/2014 | Nauman | A61F 2/28 623/23.5 |
| 2014/0195001 A1* | 7/2014 | Grohowski, Jr. | B22F 7/06 623/23.5 |
| 2014/0207248 A1* | 7/2014 | Wang | D01D 5/0007 623/23.72 |
| 2014/0222162 A1* | 8/2014 | Seedhom | A61L 27/3804 623/23.72 |
| 2014/0243995 A1* | 8/2014 | Kolewe | A61L 27/18 623/23.72 |
| 2014/0257513 A1* | 9/2014 | Monaghan | A61L 27/04 623/23.51 |
| 2014/0328999 A1* | 11/2014 | Aizenberg | A61L 27/56 427/2.26 |
| 2014/0343690 A1* | 11/2014 | Gingras | A61F 2/08 623/23.72 |
| 2014/0358238 A1* | 12/2014 | Teoh | A61F 2/2875 623/17.19 |
| 2015/0150681 A1* | 6/2015 | Ricci | A61L 27/54 623/23.51 |
| 2015/0230912 A1* | 8/2015 | Lee | B29C 67/0055 623/23.72 |
| 2015/0238318 A1* | 8/2015 | McCullen | A61F 2/30756 623/14.12 |
| 2015/0282946 A1* | 10/2015 | Hunt | A61F 2/28 623/17.16 |
| 2015/0289979 A1* | 10/2015 | Gabele | A61L 27/446 623/23.55 |

OTHER PUBLICATIONS

Strocchi et al., "Bone regeneration with calcium sulfate: evidence for increased angiogenesis in rabbits", J Oral Implantol. 2002, 28:273-8.

Goetz et al., "3D-Printed tricalcium phosphate scaffolds with temporary calcium sulfate filler", AADS/CADR Annual Meeting and Exhibition, Tampa, Florida, 2012, retrieved from the internet: http://www-personal.umich.edu/~sbayne/DMG/DMG-Publications/IADR-AADR-Meeting-Program-Books/2012-AADR-Tampa/2012-AADR-Tampa.

Chen et al., "Microstructure design of biodegradable scaffold and its effect on tissue regeneration", Biomaterials, 2011, 1-12.

Fu et al., "Direct ink writing of highly porous and strong glass scaffolds for load-bearing bone defects repair and regeneration", Acta Biomater, 2011, 7:3547-54.

Kim et al., "Stereolithographic bone scaffold design parameters: osteogenic differentiation and signal expression", Tissue Eng Part B Rev., 2010, 6:523-39.

Lee et al., :Evaluating cell proliferation based on internal pore size and 3D scaffold architecture fabricated using solid freeform fabrication technology, J Mater Sci Mater Med, 2010, 21:3195-3205.

LeGeros, "Properties of osteoconductive biomaterials: calcium phosphates.", Clin Orthop Relat Res, 2002, 395:81-98.

Nadkarni et al., "Concentrated Barium Titanate Colloidal Gels Prepared by Bridging Flocculation for Use in Solid Freeform Fabrication", J Am Ceram Soc, 2006, 89:96-103.

Thomas et al., "Calcium sulfate: Properties and clinical applications", J Biomed Mater Res, 2009, 597-610.

Ricci et al., "Three-Dimensional Printing of Bone Repair and Replacement Materials: Impact on Craniofacial Surgery", J Craniofac Surg, 2012, 23:304-308.

Simon et al., "In vivo bone response to 3D periodic hydroxyapatite scaffolds assembled by direct ink writing", J Biomed Mater Res, 2007, 83:747-758.

Simon et al., "MicroCT analysis of hydroxyapatite bone repair scaffolds created via three-dimensional printing for evaluating the effects of scaffold architecture on bone ingrowth", J Biomed Mater Res, 2008, 83:371-377.

Sohn et al., "Spontaneous healing capacity of rabbit cranial defects of various sizes", J Periodontal Implant, 2010, 40:180-187.

Costa et al., "On the Role of Subtype Selective Adenosine Receptor Agonists During Proliferation and Osteogenic Differentiation of Human Primary Bone Marrow Stromal Cells", Journal of Cellular Physiology, vol. 226, No. 5, 2011, pp. 1353-1366.

Dellinger et al., "Bone Response to 3D Periodic Hydroxyapatite Scaffolds With and Without Tailored Microporosity to Deliver Bone Morphogenetic Protein 2", Journal of Biomedical Materials Research Part A, vol. 76, No. 2, Feb. 2006, pp. 366-376.

Michna et al., "Concentrated Hydroxyapatite Inks for Direct-write Assembly of 3-D Periodic Scaffolds", Biomaterials, vol. 26, No. 28, Oct. 2005, pp. 5632-5639.

Parkinson et al., "Characterisation of Trabecular Bone Structure, in: Skeletal Aging and Osteoporosis", Skeletal Aging and Osteoporosis, Available Online at: https://rd.springer.com/chapter/10.1007/8415_2011_113, Jan. 12, 2012, pp. 31-51.

Sherwood et al., "A Three-dimensional Osteochondral Composite Scaffold for Articular Cartilage Repair", Biomaterials, vol. 23, No. 24, Dec. 2002, pp. 4739-4751.

Smay et al., "Colloidal Inks for Directed Assembly of 3-D Periodic Structures", Langmuir, vol. 18, No. 14, Jun. 14, 2002, 9 pages.

* cited by examiner

Small Pore Scaffold:

Large Pore Scaffold

TISSUE REPAIR DEVICES AND SCAFFOLDS

CROSS REFERENCE TO RELATED APPLICATIONS

This application is the National Stage of International Application No. PCT/US2013/043336, filed May 30, 2013, which claims the benefit of priority to U.S. Provisional Application No. 61/653,019, filed May 30, 2012, the disclosures of which are herein incorporated by reference in their entireties. Applicants claim the benefit of 35 U.S.C. § 120 as to the PCT application and the United States provisional application.

FIELD OF THE INVENTION

The present invention relates to multiphasic, three-dimensionally printed, tissue repair devices or scaffolds useful for promoting bone growth and treating bone fracture, defect or deficiency, methods for making the same and methods for promoting bone growth and treating bone fracture, defect or deficiency using the same.

BACKGROUND OF THE INVENTION

Bone and soft tissue defects, in the craniofacial, plastic surgery, and orthopaedic arenas are often filled using autogenous tissue grafts, processed human allograft materials, or alloplastic (synthetic) materials, all of which have deficiencies. Autogenous materials must be harvested from another surgical site, and processed human allografts are expensive, inconsistent, and may pose the risk of disease transmission. Alloplastic materials sometimes perform poorly, are sometimes long lasting or permanent, and can become infected. All of these materials have to be shaped to fit complex sites or are granular in form and must somehow be fixed in place. The search continues for a perfect bone repair material—one that can be custom fabricated to fit complex defects, will stimulate bone repair to fill large bone defects, and will eventually dissolve and/or remodel away leaving only regenerated bone. Some alloplastic materials available for similar uses include those described by Owen et al., *JBMR Part A* 2010, Chen et al. *Biomaterials* 2011, Kim et al., *Tiss Eng Part B,* 2010 and Fu et al., *Acta Biomaterialia* 2011.

Children requiring complex craniofacial repair, like those with alveolar clefts or with Treacher-Collin's syndrome, unlike adults, require fully resorbable materials that can enable bone regeneration in conjunction with craniofacial growth. With bone grafting insufficient to repair these defects, these children require innovation in bone repair technologies. The ideal bone repair scaffold needs to be off-the-shelf and/or custom fabricated to fit closely the lost or missing three dimensional structure. Three dimensional foam scaffold fabrication techniques such as particulate leaching, phase separation/inversion, porogen methods, and spin casting, while controlling overall pore size distribution, do not control individual pore location, pore morphology, and pore interconnectivity; the latter being a well-documented necessity for promoting exchange of nutrients and metabolites as well as promoting conduction of bone and vascular cells through scaffolds (Lee et al., *J Mater Sci Mater Med* 2010; 21:3195-3205).

A useful three dimensional printing process, direct write (DW), as detailed by Nadkarni et al., *J Am Ceram Soc* 2006; 89:96-103 is based on the extrusion/deposition of colloidal inks as continuous filaments. DW requires minimal processing aids (i.e., polymers) in the ink for self-supporting filament/struts that will enable printing of the lattice structures required for bone scaffolds. The scaffolds are printed by ink extrusion on the XY plane, "writing" the bottom layer, then moving up in Z height to write additional layers until a three dimensional structure is formed. Post-processing of the printed green bodies requires binder burnout and sintering in a high temperature furnace. The resulting scaffolds are of high resolution and very reproducible.

Previous work by Simon et al., *J Biomed Mater Res* 2007; 83A: 747-758, consisted of filling rabbit calvarial trephine defects of 11 mm with hydroxyapatite (HA). It is possible to increase scaffold resorption by adding, beta-tricalcium-phosphate (βTCP) to the HA to form a biphasic colloid which has been shown to be osteoconductive and remodelable. Furthermore, calcium sulfate (CS) has been added to fill the space between struts as temporary filler. CS is known to be completely resorbable, osteoconductive, angiogenic, and biocompatible (Thomas et al., *J Biomed Mater Res* 2009; 88B:597-610), and in scaffolds serves to act as a filler that dissolves just ahead of the bone ingrowth front.

It would be useful to determine how mesopore space and strut patterns determine the morphology of ingrowing bone. Although many studies have been conducted to investigate the relationship between pore size and bone formation, the optimal pore size is unclear with most studies suggesting a range of 100 to 400 µm (LeGeros, *Clin Orthop Relat Res* 2002; 395:81-98). DW allows the production of controlled mesopore sizes in scaffolds. One previous scaffold design for calvaria defects consisted of an 11 mm disk with quadrants comprising different lattice spacings ranging from 250 µm to 400 µm. After 8 and 16 weeks in vivo the smaller-pore regions produced a different pattern of bone growth and scaffold resorption than the larger-pore regions (Ricci et al., *J Craniofac Surg* 2012; 23:00-00; Ricci et al., "Biological Mechanisms of Calcium Sulfate Replacement by Bone." In: Bone Engineering, ed. JE Davies, $Em^2$ Inc., Toronto, Ont. Canada, Chapter 30, 332-344, 2000).

The many clinical situations that require extensive complex bone repair and regeneration continue to represent problems without acceptable solutions. The current clinical treatments are compromises that require elaborate and complex autogenous grafting procedures, or they represent imperfect allogeneic or alloplastic treatment options. In all cases these complex bone repair situations require that materials not made for a specific site are fit as well as possible into the defect. It would be desirable to provide new means for printing three dimensional scaffolds composed of osteoconductive biomaterials that have the potential to be custom-fabricated to repair complex defects.

SUMMARY OF THE INVENTION

In a first aspect, the present invention provides a tissue repair device or scaffold having a porous bone ingrowth area containing interconnected struts surrounded by a microporous shell. The microporous shell may function to attach but limit soft tissue ingrowth. At the ends of the tissue repair device or scaffold, the shell may be extended as a guide flange to stabilize the tissue repair device or scaffold between ends of bone, across a bone defect, etc. or the tissue repair device or scaffold may be used to repair a defect of a flat bone. The center of the tissue repair device or scaffold may be empty and may serve as a potential marrow space. The porous ingrowth structure may be infiltrated with a soluble filler or carrier, such as, for example calcium sulfate. This soluble filler or carrier, such as, for example calcium sulfate, may be infiltrated with one or more of an antibiotic, a growth factor, a differentiation factor, a cytokine, a drug, or a combination of these agents. The tissue repair device or scaffold may fit between the cortical bone ends of long bone and conduct healing bone, which arises largely from the endosteal and periosteal surfaces or it may be used at or near a bone defect of, for instance, flat bone. The tissue repair device or scaffold may be stabilized using a modified bone plate or bone screws. The tissue repair device or scaffold may be produced by a three dimensional printing procedure and may be formed of, for instance, an osteoconductive ceramic.

The tissue repair device or scaffold may be a multiphasic, three-dimensionally printed, tissue repair device. The struts may be substantially cylindrical and they may be, for instance, from about 1-1,000, 10-900, 20-800, 30-700, 40-600, 50-500, 60-400, 100-350, 120-300, or about 200-275 μm diameter. In some embodiments, the struts may be about 20-940 μm diameter. In some embodiments the struts are within about 3×, 2× or 1.5× or substantially the same diameter as bone trabeculae. In some embodiments, the struts may be separated longitudinally by a space of up to 100, 200, 300, 400, 500, 600, 700, 800, 900 μm or more, or even 1.0 mm or more. Similarly, the tissue repair device or scaffold may be porous having mesopores that may be present in a size generally less than about 100, 75, 50, 30, 20, 10 or even less than about 5, 4, 3, 2, 1, or even 0.5, 0.4, 0.3, 0.2 or 0.1 μm diameter. The struts may be arranged in a substantially linear arrangement. The tissue repair device or scaffold may be substantially resorbable so that, for instance, after about 8, 10, 12, 16, 18, 20, 24 or so weeks presence in vivo, about 5, 10, 15, 20, 25, 30, 35, 40, 45, or 50% or more of the tissue repair device or scaffold may be resorbed. The tissue repair device or scaffold may be at least about 50%, 60%, 70%, 75%, 80%, 85%, 90%, 95% or even more porous. Similarly, the tissue repair device or scaffold may be efficient to encourage and provide bone growth such that after about 8 or 16 weeks presence in vivo, about 5, 10, 15, 20, 25, 30, 35, 40, 45, or 50% or more of the tissue repair device or scaffold may be replaced by bone. The tissue repair device or scaffold may promote or form cancellar or cortical bone, within the tissue repair device or scaffold or in the region or area of the tissue repair device or scaffold. The tissue repair device or scaffold may be used to remodel bone or to regionally control the density of bone.

The tissue repair device or scaffold may feature a gradient of mesopores formed by varying strut spacing in three dimensions (X, Y, and Z). Spacing in the X and Y dimensions may be accomplished using radial or V-shaped patterns with spacing from, for instance, 100-940 μm. Spacing in the Z dimension may be accomplished by stacking multiple layers of the radial struts. The porous ingrowth structure may be infiltrated with a soluble filler or carrier, such as, for example calcium sulfate. In some embodiments, the porous ingrowth structure may be infiltrated with a filler that attracts osteoclasts, such as, for example calcium phosphate mineral and type I collagen protein. In some instances, the printed tissue repair device or scaffold s may be micro/nanoporous on about a 0.1-1 μm pore size level. The pores then may in some instances be infiltrated with solubilized collagen.

The tissue repair device or scaffold may be effective for promoting bone growth and treating bone fracture, defect or deficiency across a distance of at least 5, 10, 11, 12, 13, 14, 15, 18, 20, 25, 30, 35, 40, 50, 60, 70, 80, 90 or 100 or more millimeters. Similarly, the tissue repair device or scaffold may be effective for promoting the growth of both cortical or cortical-like bone and trabecular or trabecular-like bone. The bone so grown may be in any suitable proportion, such as, for example 95%, 90%, 80%, 75%, 70%, 60%, 50%, 40%, 30%, 25%, 20%, 10% or so trabecular or trabecular-like bone, or just the opposite, i.e. 95%, 90%, 80%, 75%, 70%, 60%, 50%, 40%, 30%, 25%, 20%, 10% or so cortical or cortical-like bone. The tissue repair device or scaffold may be effective for reducing or shortening the normal repair time across a bone defect by 5, 10, 20, 25, 30, 40, 50, 75, 90% or more. In some instances, the bone defect may be repaired in about half, one third or one quarter of the normally required period of time. In many instances, the larger pore sizes are found near the outer portions of the scaffold and the smaller pore sizes are found near the inner portions of the scaffold. In some instances, the portion of the scaffold forming the inner half of the surface area may have a median pore diameter size or area that is 5, 10, 20, 25, 30, 40, 50, 75, 90% or more smaller than the median pore diameter size or area of the portion of the scaffold forming the outer half of the surface area. In some instances the pore sizes are arranged architecturally in any suitable or desirable configuration so as to customize the type of bone growth, for instance bone density, trabecular-like bone or cortical-like bone, desired. Similarly, in some instances, the tissue repair device or scaffold is formed and shaped to customize the shape of tissue or bone repair desired to optimally span a defect. Further, in some instances, a portion of the tissue repair device or scaffold may be substantially hollow, for instance, 10, 20, 25, 30, 40, 50, 75, 90% or more of the interior portion of the tissue repair device or scaffold may be substantially hollow.

In a second aspect, the present invention provides a method for promoting bone growth or treating bone fracture, defect or deficiency by providing a tissue repair device or scaffold having a porous bone ingrowth area containing interconnected struts surrounded by a microporous shell. The promoting bone growth or treating bone fracture, defect or deficiency may feature controlling or affecting the density of bone or may feature remodeling bone, for instance, cancellar or cortical bone. In most instances the tissue repair device or scaffold is provided in vivo to a region featuring a bone deficiency, fracture or void. The microporous shell may function to attach but limit soft tissue ingrowth. At the ends of the tissue repair device or scaffold, the shell may be extended as a guide flange to stabilize the tissue repair device or scaffold between ends of bone. The center of the tissue repair device or scaffold may be empty and may serve as a potential marrow space. The porous ingrowth structure may be infiltrated with a soluble filler or carrier, such as, for example calcium sulfate. This soluble filler or carrier, such as, for example calcium sulfate, may be infiltrated with one or more of an antibiotic, a growth factor, a differentiation factors, a cytokine, a drug, or a combination of these agents. The tissue repair device or scaffold may fit between the cortical bone ends of long bone and conduct healing bone, which arises largely from the endosteal and periosteal surfaces. The tissue repair device or scaffold may be stabilized using a modified bone plate or bone screws. The tissue repair device or scaffold may be produced by a three dimensional printing procedure and may be formed of, for instance, an osteoconductive ceramic.

The tissue repair device or scaffold may be a multiphasic, three-dimensionally printed, tissue repair device. The struts may be substantially cylindrical and they may be, for instance, from about 1-1,000, 10-900, 20-800, 30-700, 40-600, 50-500, 60-400, 100-350, 120-300, or about 200-275 μm diameter. In some embodiments the struts are about 20-940 μm diameter. In some embodiments the struts are within about 3×, 2× or 1.5× or substantially the same diameter as bone trabeculae. In some embodiments, the struts may be separated longitudinally by a space of up to 100, 200, 300, 400, 500, 600, 700, 800, 900 μm or more, or even 1.0 mm or more. Similarly, the tissue repair device or scaffold may be porous having mesopores that may be present in a size generally less than about 100, 75, 50, 30, 20, 10 or even less than about 5, 4, 3, 2, 1, or even 0.5, 0.4, 0.3, 0.2 or 0.1 μm diameter. The struts may be arranged in a substantially linear arrangement. The tissue repair device or scaffold may be substantially resorbable so that, for instance, after about 8, 10, 12, 16, 18, 20, 24 or so weeks presence in vivo, about 5, 10, 15, 20, 25, 30, 35, 40, 45, or 50% or more of the tissue repair device or scaffold may be resorbed. The tissue repair device or scaffold may be at least about 50%, 60%, 70%, 75%, 80%, 85%, 90%, 95% or even more porous. Similarly, the tissue repair device or scaffold may be efficient to encourage and provide bone growth such that after about 8 or 16 weeks presence in vivo, about 5, 10, 15, 20, 25, 30, 35, 40, 45, or 50% or more of the tissue repair device or scaffold may be replaced by bone.

The tissue repair device or scaffold may feature a gradient of mesopores formed by varying strut spacing in three dimensions (X, Y, and Z). Spacing in the X and Y dimensions may be accomplished using radial or V-shaped patterns with spacing from, for instance, 100-940 μm. Spacing in the Z dimension may be accomplished by stacking multiple layers of the radial struts. The porous ingrowth structure may be infiltrated with a soluble filler or carrier, such as, for example calcium sulfate. In some embodiments, the porous ingrowth structure may be infiltrated with a filler that attracts osteoclasts, such as, for example calcium phosphate mineral and type I collagen protein. In some instances, the printed tissue repair device or scaffolds may be micro/nanoporous on about a 0.1-1 μm pore size level. The pores then may in some instances be infiltrated with solubilized collagen.

The tissue repair device or scaffold may be effective for promoting bone growth and treating bone fracture, defect or deficiency across a distance of at least 5, 10, 11, 12, 13, 14, 15, 18, 20, 25, 30, 35, 40, 50, 60, 70, 80, 90 or 100 or more millimeters. Similarly, the tissue repair device or scaffold may be effective for promoting the growth of both cortical or cortical-like bone and trabecular or trabecular-like bone. The bone so grown may be in any suitable proportion, such as, for example 95%, 90%, 80%, 75%, 70%, 60%, 50%, 40%, 30%, 25%, 20%, 10% or so trabecular or trabecular-like bone, or just the opposite, i.e. 95%, 90%, 80%, 75%, 70%, 60%, 50%, 40%, 30%, 25%, 20%, 10% or so cortical or cortical-like bone. The tissue repair device or scaffold may be effective for reducing or shortening the normal repair time across a bone defect by 5, 10, 20, 25, 30, 40, 50, 75, 90% or more. In some instances, the bone defect may be repaired in about half, one third or one quarter of the normally required period of time. In many instances, the larger pore sizes are found near the outer portions of the scaffold and the smaller pore sizes are found near the inner portions of the scaffold. In some instances, the portion of the scaffold forming the inner half of the surface area may have a median pore diameter size or area that is 5, 10, 20, 25, 30, 40, 50, 75, 90% or more smaller than the median pore diameter size or area of the portion of the scaffold forming the outer half of the surface area. In some instances the pore sizes are arranged architecturally in any suitable or desirable configuration so as to customize the type of bone growth, for instance bone density, trabecular-like bone or cortical-like bone, desired. Similarly, in some instances, the tissue repair device or scaffold is formed and shaped to customize the shape of tissue or bone repair desired to optimally span a defect.

In a third aspect, the present invention provides a method for producing a tissue repair device or scaffold useful for promoting bone growth or treating bone fracture, defect or deficiency having a porous bone ingrowth area containing interconnected struts surrounded by a microporous shell. The method features (a) providing a microporous shell that may function to attach but limit soft tissue ingrowth, (b) infiltrating a porous ingrowth structure with a soluble filler or carrier, and optionally (c) infiltrating the porous ingrowth structure with one or more of an antibiotic, a growth factor, a differentiation factor, a cytokine, a drug, or a combination of these agents. The soluble filler or carrier may be a filler that attracts osteoclasts, such as, for example calcium phosphate mineral and type I collagen protein. tissue repair device or scaffold useful for promoting bone growth or treating bone fracture, defect or deficiency having a porous bone ingrowth area containing interconnected struts surrounded by a microporous shell may have the features described herein with respect to the first and second aspects of the invention.

DETAILED DESCRIPTION OF THE INVENTION

Multiphasic, three-dimensionally printed, tissue repair device (M3DRD) scaffolds may be used to replace current bone grafting techniques and bone graft substitutes, all of which have serious drawbacks and cannot be produced in the complex designs and shapes necessary for repair of complex bone defects. M3DRDs can be custom produced for complex grafting applications for craniofacial and orthopaedic bone repair.

Figure 1:
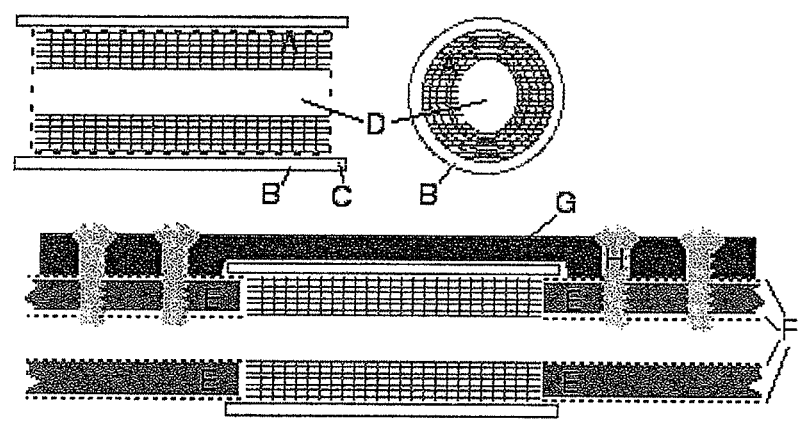
FIG. 1 is a schematic drawing of a tissue repair device or scaffold design that may be used to regenerate a long bone defect, showing its placement and fixation in the defect. The scaffold has a porous bone ingrowth area (A) containing interconnected 250 μm cylindrical struts surrounded by a microporous shell (B) to attach but limit soft tissue ingrowth. At the ends of the scaffold, the shell may be extended as a guide flange (C) to stabilize the construct between the bone ends. The center of the scaffold (D) may be left empty as a potential marrow space. The porous ingrowth structure (outlined with dashed line in upper left drawing) may be infiltrated with a soluble filler/carrier (such as calcium sulfate as an example) that may be infiltrated with one or more of antibiotic, growth factors, differentiation factors, cytokines, drugs, or a combination of these agents. The scaffold may fit between the cortical bone ends (E) of the long bone and conduct healing bone, which arises largely from the endosteal and periosteal surfaces (F). The construct may be stabilized using a modified bone plate (G) and bone screws (H).

The multiphasic, three-dimensionally printed, tissue repair device (M3DRD) is a device beginning with at least one component, and possibly comprising three or more components (FIG. 1). The main components are (1) the scaffold, (2) the temporary filler/carrier material, and (3) a bioactive molecule/drug contained in the filler/carrier.

The Scaffold

Figure 2:
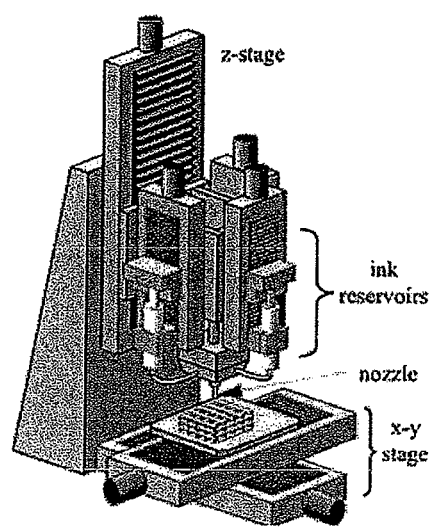
FIG. 2 depicts a direct write (DW) printing apparatus based on the extrusion/deposition of colloidal inks as continuous filaments. DW requires minimal processing aids (i.e., polymers) in the ink for self-supporting filament/struts that will enable printing of the lattice structures required for bone scaffolds. The scaffolds are printed by ink extrusion on the XY plane, "writing" the bottom layer, then moving up in Z height to write additional layers until a three dimensional structure is formed. Post-processing of the printed green bodies requires binder burnout and sintering in a high temperature furnace. The resulting scaffolds are of high resolution and very reproducible.
Figure 3:
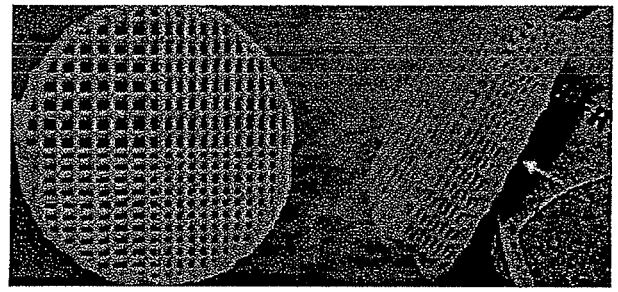
FIG. 3 depicts one previous scaffold design for calvaria defects having an 11 mm disk with quadrants having different lattice spacings ranging from 250 μm to 400 μm. After 8 and 16 weeks in vivo the smaller-pore regions produced a different pattern of bone growth and scaffold resorption than the larger-pore regions

The core of the M3DRD is a three-dimensional scaffold that may be produced using a 3-D printing technique referred to as robotic deposition or direct write (DW) technology (See, FIG. 2). This technique uses a computer controlled printing process and colloidal inks to form three-dimensional structures. These structures can form on the self components or can be custom formed for filling individual bone defects from tomographic data (X-ray, sonographic or MRI).

Ink fabrication and the printing system itself are described in more detail in other references, but basically the system uses water-based rheologically controlled inks that become solid as they leave the print nozzle. These inks consist of finely controlled ceramic particles in a water-based slurry containing organic chemicals that control the handling characteristics of the colloidal ink. This allows 3-D lattice-like structures to be printed, in layers, without or with minimal sag of unsupported structural elements.

Using this system, the elements of the first layer may be printed by forcing the ink through a small (~50-400 µm diameter) nozzle onto a support plate, using the x and y coordinate control system of an x-y-z control gantry system. Then the z control system is used to move the nozzle up slightly less than 1 nozzle diameter. Then the next layer is printed over the first layer. This is continued layer-by-layer until the entire 3-D structure is finished.

The entire structure may be printed in an oil bath to prevent drying. The system may have 3 nozzles and ink reservoirs so that up to three materials can be used to print a single structure. Fugitive inks, inks consisting entirely of material that burn off during firing, may also be used as part of the printing process. These can be used to print support structures for complex parts requiring temporary supports.

The resulting structures are then removed from the oil bath, dried, and fired in a programmable furnace to produce the final ceramic structure. Firing is currently done at approximately 1100° C. for about four hours, which substantially burns off the organic components, sintering the ceramic particles together into a solid structure. This may cause a small amount of predictable shrinkage that can be calculated into the printing process to produce precise and predictable structures.

The print nozzles may be routinely cylindrical producing cylindrical rod printed structures. However, nozzles may be made that are shaped to produce non-cylindrical structures or structures with surface striations of sizes designed to control cell migration, growth, and differentiation based on our earlier surface modification patents. (See, U.S. Pat. No. 6,419,491)

Composition

Calcium phosphate base scaffold were made from inks based upon permanent, remodelable (through bone remodeling processes), or soluble materials, or some combination of these. Some promising materials at this time are hydroxyapatite (HA) ceramics, tricalcium phosphate ceramics (TCP), and biphasic ceramics (HA/TCP) having a combination of the two materials. The HA materials produce permanent or very long-lasting scaffolds (depending on firing temperatures), the HA/TCP combinations may be varied with high HA percentages producing long-lasting scaffolds, and ~99% TCP/1% HA scaffolds have been used to produce scaffolds that have been shown to remodel significantly through osteoclastic activity. Some such scaffolds contain approximately 3 mm thick, 11 mm diameter porous disks, with varying pore structures in different regions of the disk, and about a 0.5 mm thick solid cap structure of about 12 mm diameter. These have been inserted into 11 mm diameter trephine holes in rabbit parietal (skull) bones to test the bone and soft tissue response. It was demonstrated that these scaffolds can effectively be produced to have combinations of solid shell components to restrict fibrous tissue infiltration, and internal lattice structures with 270 µm diameter elements (this diameter can be varied using nozzle size) and pores (mesopores) ranging in size from less than 100 µm to 1000 µm in largest dimension. These constructs, with pores and strut sizes above the micron scale and below millimeter scale are referred to as mesostructures. The lattice structures, because of the HA and TCP composition, promote osteoconduction of new bone into the scaffolds. By adding small organic particles to the inks, microporous (on a submicron to ~20 µm pore size) scaffold components can also be produced. These can be designed to attach fibrous connective tissue. Using these combinations of solid layers, various size open-weave mesopore lattices, microstructured lattice elements, and microporous lattice elements, complex structures can be designed and fabricated to conduct the ingrowth and formation of bone, marrow tissue, fibrous tissue, and blood vessels. An example of a scaffold for long bone regeneration is shown in FIG. 1. Since the DW system can print more than one material in a scaffold, it is feasible to print scaffolds with permanent HA components as well as remodelable TCP elements. This may be applicable in orthopaedic applications where long-term strength of the scaffold is necessary.

The Scaffold Filler/Carrier Material and Bioactive Factors

This filler/carrier component has a cement, polymer, or organic/natural hydrogel-based material that may be used to infiltrate the scaffold to produce a solid or nearly solid (if the filler is microporous) composite structure. This filler/carrier material may be soluble at some known or controlled rate, provide the scaffold with greater initial mechanical strength and stability, and then dissolve to allow and/or stimulate bone or soft tissue ingrowth (depending on the application and design). The filler/carrier may dissolve from the outside of the scaffold inward to its center, allowing the composite to become porous, as the scaffold component is exposed, and as tissue and blood vessels grow in from the surrounding tissue. This component may also protect the internal portion of the scaffold from the formation of a blood clot that may normally form there during early healing. This blood clot may become infected in oral and craniofacial sites where these sites are often non-sterile, or may become a granulation/fibrous tissue or necrotic either of which can impede bone ingrowth. The filler/carrier material may inherently stimulate tissue formation, or it may contain incorporated drugs, growth factors, cytokines, or antibiotics.

Some exemplary filler/carrier materials are calcium sulfate (plaster of paris), timed release calcium sulfate (a slow-dissolution version of calcium sulfate), and chitosan, a derivative of chitin, a biologically-derived polysaccharide, that can be used as a coating or hydrogel filler. Other materials, such as resorbable polymers like pol(L-lactic acid) (PLLA), may be used as filler/carrier materials, but alternatively these may be used as a coating material for the scaffold rather than filler. As such, they can still strengthen the scaffold and act as release materials, but may not be utilized to fill the scaffold and make it a solid structure.

Calcium sulfate was used as a filler and as a drug carrier material, where it was found to enhance mechanical properties of the structures, release biologically active agents in a predictable way, and not interfere with bone formation. Bioactive molecules investigated using this carrier include recombinant Platelet derived Growth Factor (PDGF) and Bone Morphogenetic Protein (BMP).

Using Scaffold Mesostructure to Control Scaffold Mechanical Characteristics, Bone Characteristics, and Scaffold Remodeling It is possible to design and produce scaffolds with mechanical properties suitable for use in craniofacial bone repair, and which, with some external support, are appropriate for orthopaedic repair. Scaffold mesostructure may also be used to control the structural characteristics and density of bone that is conducted into the scaffolds. Using a rabbit 11 mm diameter trephine defect as a model, three different design scaffolds were produced to fill the defects and examine bone regeneration. All scaffolds were produced of the same material, 99% TCP 1% HA ceramic, and were made of the same sized printed struts that were 270 µm in diameter. All scaffolds were also filled with medical grade calcium sulfate, and started as solid structures. Mesostructure was varied using strut spacing in the layers of the scaffold (x and y directions) and by stacking struts in the z direction. One type of scaffold that contained three strut spacings that produced open pores that were referred to (in the x and y directions) as 250×250 µm, 250×400 µm, and 400×400 µm size pores was produced (these dimensions are approximate). "Z" spacing was slightly less than one strut in height, or 230 µm. As measured by microcomputed tomography, these three zones had scaffold volume percentages of 46, 56, and 70%.

Two scaffolds were produced that had continuously variable porosity produced using radial struts alternating with concentric rings of different spacings. One scaffold had layers of 1 z and 2 z spacing and ring-shaped regions with scaffold volumes ranging from 55 to 94%. The other scaffold had 3 z spacing and regions ranging from 41 to 56% volume. Thus, a range of scaffold volumes were tested ranging from 41 to 94% scaffold. In all scaffolds, bone was capable of consistently growing to the center of the defect (across 5.5 mm distance) by 8 weeks.

This extent of consistent bone infiltration has not been observed in other osteoconductive scaffolds, and is due to the size and organization of the scaffold elements in the scaffolds. By using many small struts, in the size range of bone trabeculae, to conduct ingrowth, and by organizing them in ways that conduct bone in straight lines across the defects, it is possible to optimize the process of osteoconduction. This process, referred to as "directed osteoconduction" is novel to this type of scaffold. In scaffolds with random pore organization, the process of directed osteoconduction is not observed, and there consistent growth across large defects takes longer to occur. With the structures described herein, bone volumes at 8 and 16 weeks ranged from 9 to 40% (8 weeks) and 10 to 56% (16 weeks). Bone volume was inversely related to scaffold volume. More open (lower scaffold volume) scaffolds showed more bone ingrowth, and bone increased over time. Scaffold remodeling ranged from 5% to 56%, with more remodeling being observed in more open scaffolds at later time periods. Higher volume scaffolds (with smaller pores) produced more compact, lamellar bone, with the combination of scaffold and bone showing very little soft tissue and resembling a cortex-like structure. In contrast, lower volume scaffolds (with larger pores) produced more porous, disorganized bone, with the combination of bone and scaffold resembling cancellous bone. The type of bone adjacent to the scaffold (cortical or cancellous) at least partially influenced the bone growing in the adjacent scaffold.

Features of M3DRD Scaffolds

In all, this data shows that osteoconductive scaffolds with designed mesostructures can be made with mechanical properties suitable for a wide range of bone repair applications. These scaffolds can be used to regenerate bone across significant distances without the need for bone cell or stem cell augmentation. The observed rate of osteoconduction across large defects is due to "directed osteoconduction" based on the use of many small struts, in the size range of bone trabeculae, that are organized in straight arrays to conduct bone efficiently across large distances.

The scaffolds can also be used to control resulting bone density, structure, and scaffold remodeling rates. The M3DRD scaffolds can be designed so that they regenerate bone that microstructurally approximates or matches adjacent bone. That is, where cancellous bone is needed, it is possible to regenerate cancellous structure, and where cortical bone is needed, it is possible to regenerate that form as well. Additional features like solid cap layers may successfully prevent soft tissue ingrowth. The CS filler may temporarily enhance structural mechanical properties and not impede bone formation and prevent fibrous tissue ingrowth and infiltration by infection and allow angiogenesis to proceed.

The CS can also be used for controlled release of bioactive molecules. Use of the DW printing system allows custom design and printing of complex mesostructures with micron scale accuracy. This allows both off-the-shelf printed structures as well as custom printed M3DRD scaffolds for repair of complex defects in patients, based on MRI or CT data. This technology has widespread application in the craniofacial and orthopaedic bone repair/replacement fields.

Exemplary Tissue Repair Device or Scaffold

Bone defects are currently filled by complex autogenous grafting procedures; or imperfect allogeneic or alloplastic treatments not designed for a specific site. Direct Write (DW) fabrication allows us to print 3-D scaffolds composed of osteoconductive biomaterials, complex multicomponent biphasic (COMBI) calcium phosphate scaffolds that have the potential to be custom-fabricated to repair complex bone defects. Current literature still debates optimum and threshold pore requirements for bone regeneration. We tested scaffolds in a critical-sized (unable to close on its own) in vivomodel to study effects on bone density, extent of ingrowth, and bone/scaffold remodeling.

Scaffolds were designed with variable mesopore spacing in all (X, Y, and Z) planes. To vary pore sizes, two scaffold designs of layers of concentric circles, alternating with radial struts of 1, 2, or 3 overlapping layers in z height, were fabricated by DW from 15:85 HAP/$\beta$-TCP and sintered at 1100° C. A calcium sulfate temporary filler prevented soft tissue invasion and/or infection. Scaffolds were embedded in vivo in trephine defects. After 8-16 weeks, analysis of bone ingrowth and scaffold and bone remodeling was quantified by MicroCT (Scanco Medical) and scaffolds were embedded in polymethylmethacrylate (PMMA) then evaluated histologically with light microscope.

Scaffold volume was designed to vary by ring section. Bone volume was higher in the more open, less scaffold-dense areas. Pores ranged from around 100 to 940 microns. Bone grew into all varied height layers, but appeared to take longer to get through largest pore sizes. Pores larger than 500 microns still filled with bone well contrary to previous literature findings.

Particular scaffolds used demonstrated that three dimensional printed calcium phosphate scaffolds are capable of growing bone across at least 11 mm voids in 8 weeks. Bone can grow into pores as large as 940 µm and as small as 20 µm. Bone morphology can be trabecular-like or cortical-like depending on scaffold design. The scaffolds may be designed with regionally different biological and mechanical properties for a wide range of clinical applications.

DETAILED DESCRIPTION OF THE PREFERRED EMBODIMENTS

Example 1

Materials and Methods

Figure 4:
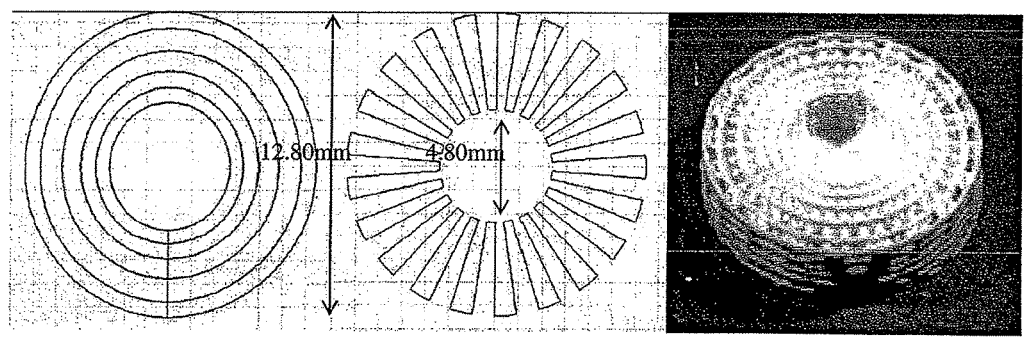
FIG. 4 depicts two scaffold architectures, (A) small-pore (SP) and (B) large-pore (LP), designed to increase the diversity of pore geometry. Both scaffolds contained a solid cap of layered parallel struts on one surface, which biologically served as a barrier to block soft tissue ingrowth from the scalp, but structurally served as a base for the printing of the scaffold lattice in the Z direction. The scaffold design built upon this base differed between the SP and LP scaffolds, but in general, consisted of a layers of nested concentric circles (CC) alternating with one or more radial (R) layers. Variation of porosity in the Z direction arose from use of 1, 2, or 3 stacks of radial layers, and porosity in the X and Y direction came from the spacing between radial struts in the same layer.
Figure 4:
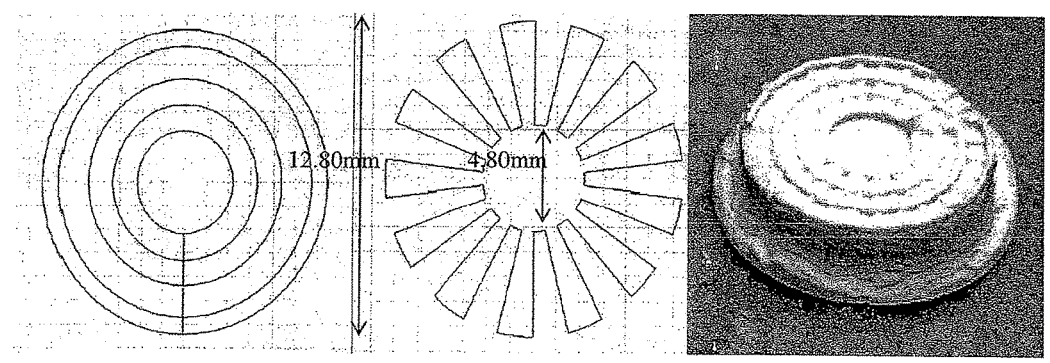
Figure 5:
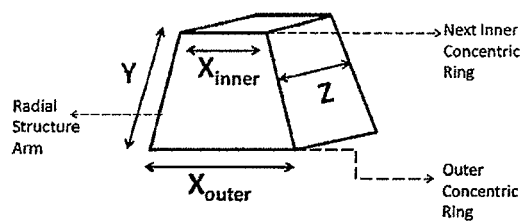
FIG. 5 provides a diagram of a unique mesopore volume formed. A ring of such volumes form the space between CC and R layers in the scaffolds described.

Two scaffold architectures, small-pore (SP) and large-pore (LP), were designed to increase the diversity of pore geometry. Both scaffolds contained a solid cap of layered parallel struts on one surface, which biologically served as a barrier to block soft tissue ingrowth from the scalp, but structurally served as a base for the printing of the scaffold lattice in the Z direction. The scaffold design built upon this base differed between the SP and LP scaffolds, but in general, consisted of a layers of nested concentric circles (CC) alternating with one or more radial (R) layers. Variation of porosity in the Z direction arose from use of 1, 2, or 3 stacks of radial layers, and porosity in the X and Y direction came from the spacing between radial struts in the same layer. The specific designs of SP and LP scaffolds are diagrammed in FIGS. 4 and 5.

Scaffolds printed with ink of 15:85 HA/$\beta$-TCP and fired at 1100° C. Scaffolds were then scanned at medium resolution in microCT (Scanco Medical) to evaluate the volume of struts and mesopores before implantation. Scaffolds were then filled with CS and a 1 mm ring of scaffold above the cap was removed with a dental drill to open the blocked radial struts in the perimeter. This left a diameter of 11 mm.

Surgical Procedure

Surgery was performed on 8 adult New Zealand White Rabbits following an Institutional Animal Care and Use Committee (IACUC) approved protocol. A 3.0 cm midsagittal incision was made through the skin and soft tissue of the dorsum of the head. Bilateral 11.0 mm diameter trephine defects were made immediately posterior to the coronal suture in the parietal bone, without dural involvement.

After placement of LP and SP scaffolds in right and left defects, respectively, the soft tissue and skin was closed with 4-0 resorbable sutures. Wounds were cleaned with sterile saline and treated with triple antibiotic ointment. No signs of infection, pain, or other complications resulted. 7 animals were euthanized after 8 weeks and 1 animal after 16 weeks.

Sample Analysis

Figure 7:
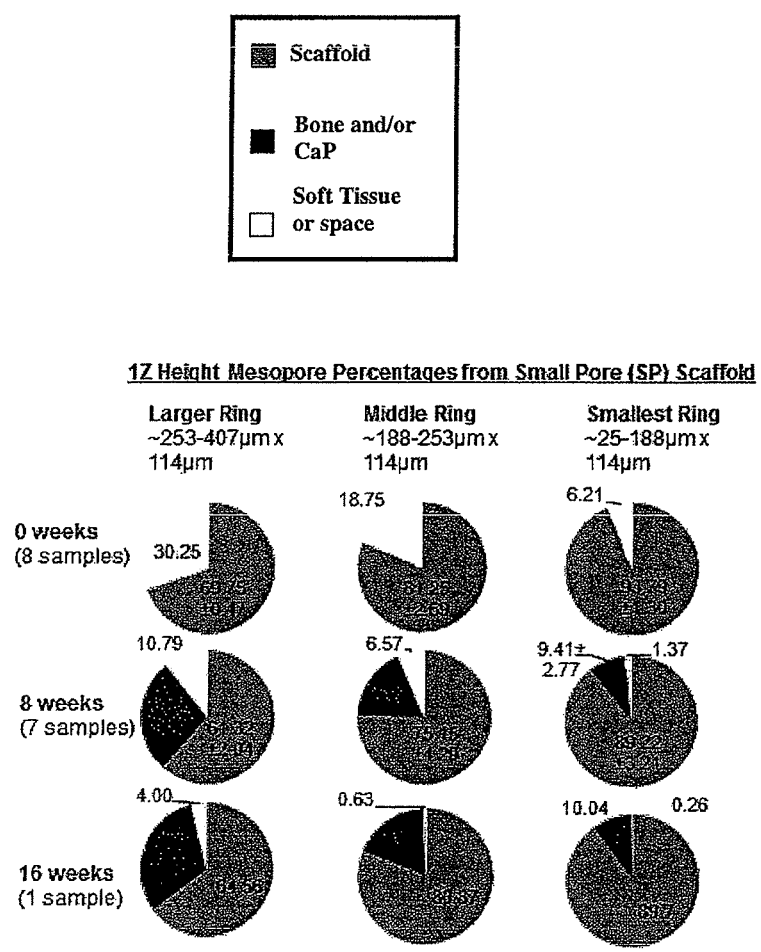
FIG. 7 provides the observed 1Z height mesopore percentages from a small pore scaffold having three ring sizes, large, middle and small, after 0, 8 and 16 weeks.
Figure 9:
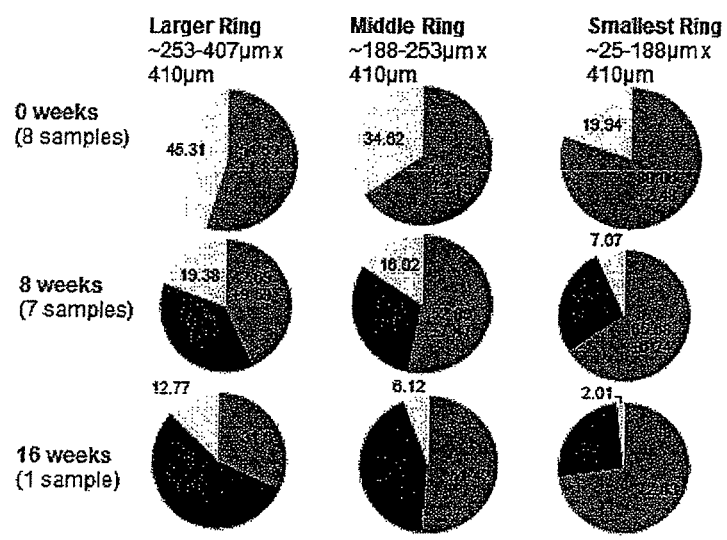
FIG. 9 provides the observed 2Z height mesopore percentages from a small pore scaffold having three ring sizes, large, middle and small, after 0, 8 and 16 weeks.
Figure 10:
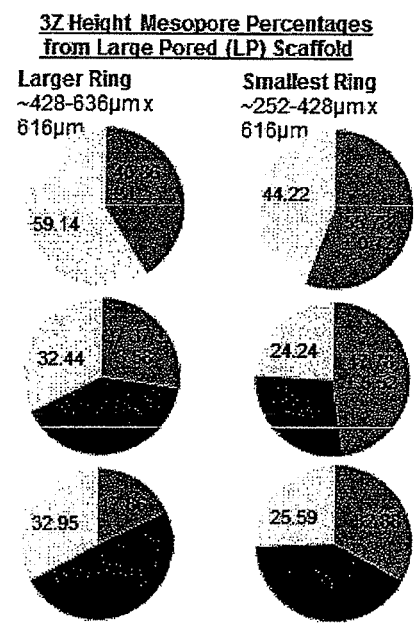
FIG. 10 provides the observed 3Z height mesopore percentages from a small pore scaffold having three ring sizes, large, middle and small, after 0, 8 and 16 weeks.
Figure 11:
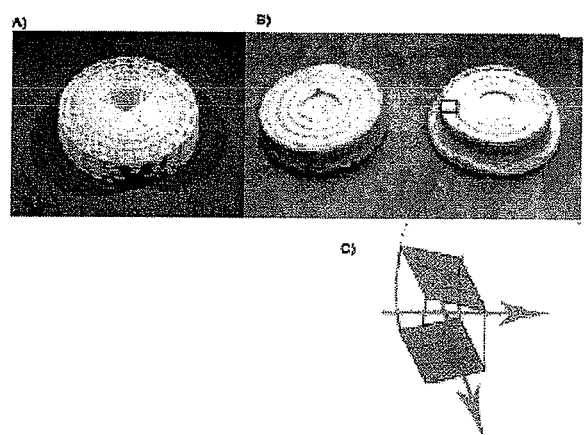
FIG. 11 depicts A) a large pore scaffold; B) a small pore scaffold, before and after removal of outer ring; and C) an enlarged diagram of an outer ring large mesopore. The rectangles correspond to the 3 layers of radial struts between concentric circles and the arrows designate the 4 open walls of the mesopore.
Figure 12:
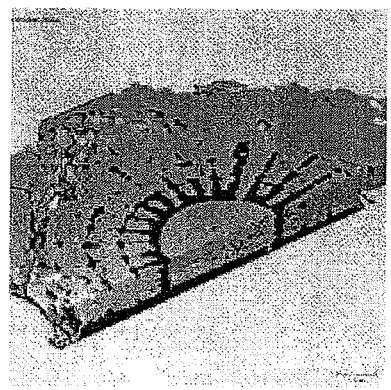
FIG. 12 provides a microCT scan of a large pore scaffold after 16 weeks. The scaffold is seen digitally sectioned both vertically through the center and horizontally between superficial and deep mesopores. The scaffold and cap appear darker, and the surrounding hard tissue appears in lighter shade.
Figure 13:
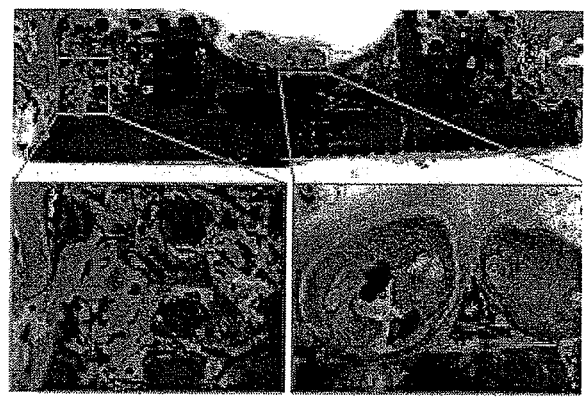
FIG. 13 shows horizontal slices from a scaffold through mesopores.
Figure 14:
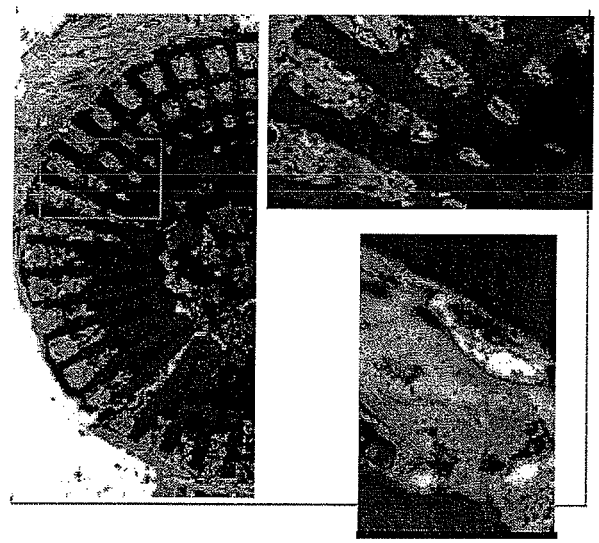
FIG. 14 provides a vertical slice through the center and horizontal slices through middle of 3Z mesopores in a scaffold.
Figure 15:
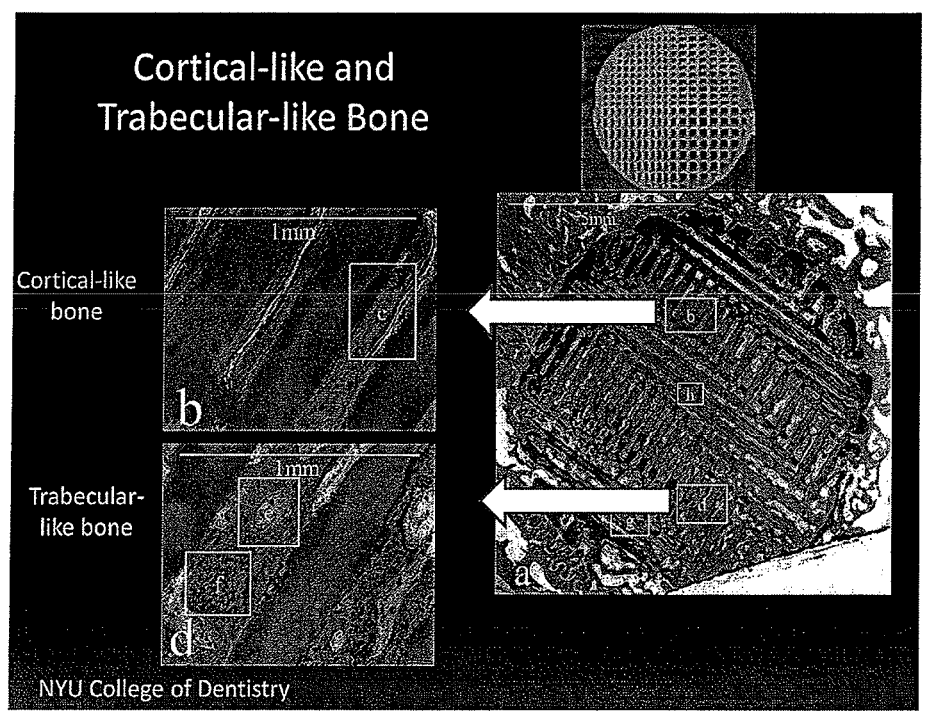
FIG. 15 provides slices through a scaffold demonstrating the growth of both cortical and trabecular bone.
Figure 16:
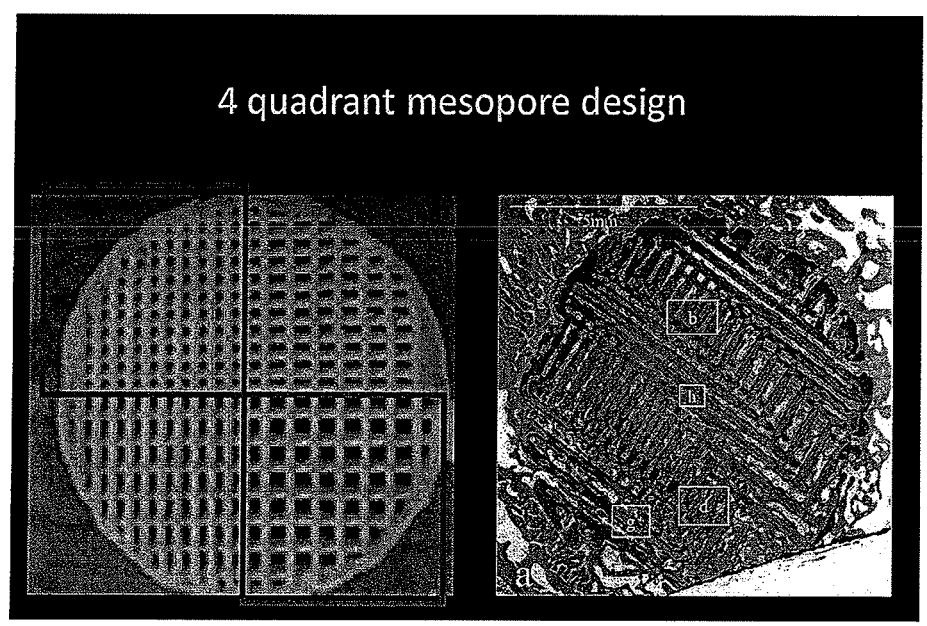
FIG. 16 depicts a scaffold having a four quadrant mesopore design having mesopores of differing sizes in distinct quadrants.
Figure 17:
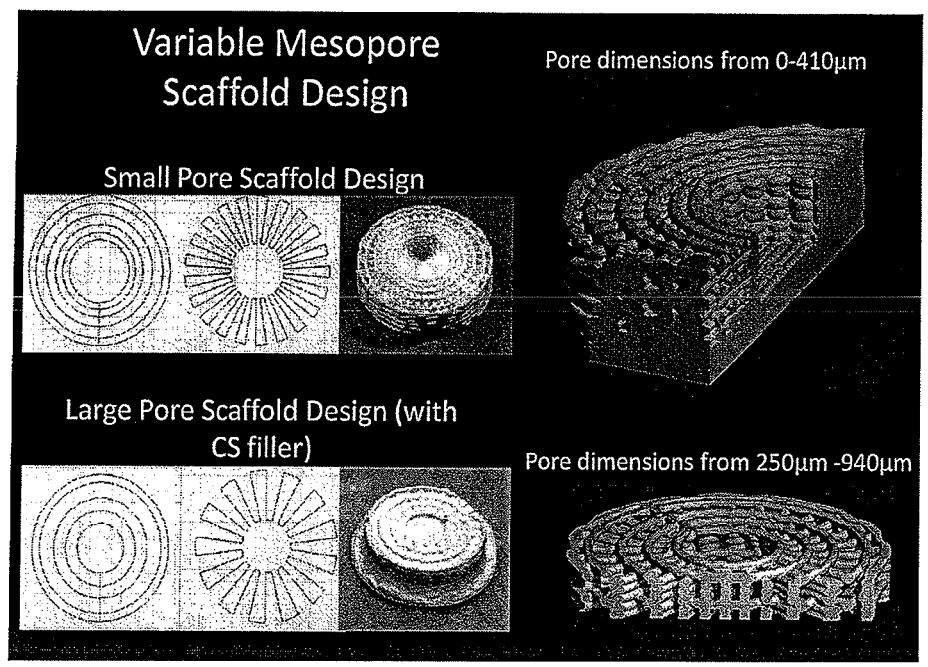
FIG. 17 depicts two scaffold architectures, (A) small-pore (SP) and (B) large-pore (LP), designed to increase the diversity of pore geometry. The small-pore design has pore dimensions of from 0-410 µm, and the large-pore design has pore dimensions of from 250-940 µm.
Figure 18:
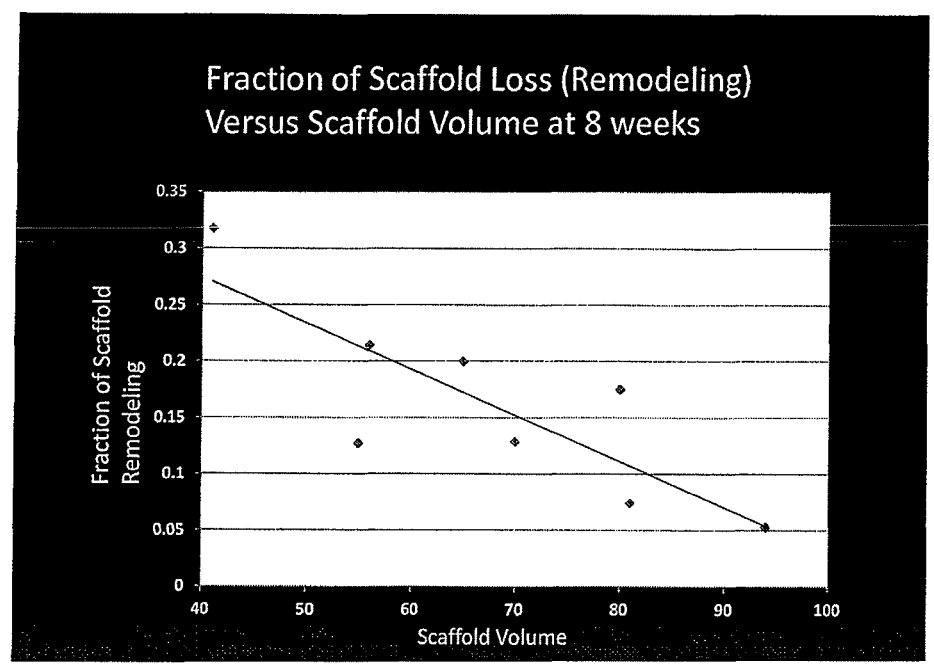
FIG. 18 graphically depicts the fraction of scaffold loss (remodeling) versus scaffold volume at 8 weeks after implant clearly demonstrating bone growth.
Figure 19:
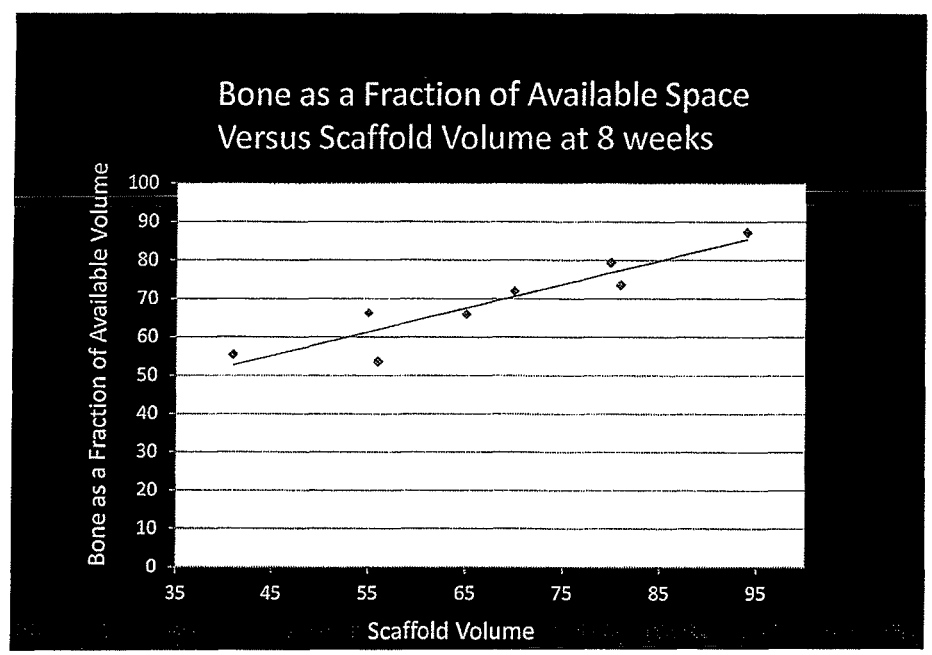
FIG. 19 graphically depicts bone as a fraction of available space versus scaffold volume at 8 weeks after implant clearly demonstrating bone growth.
Figure 20:
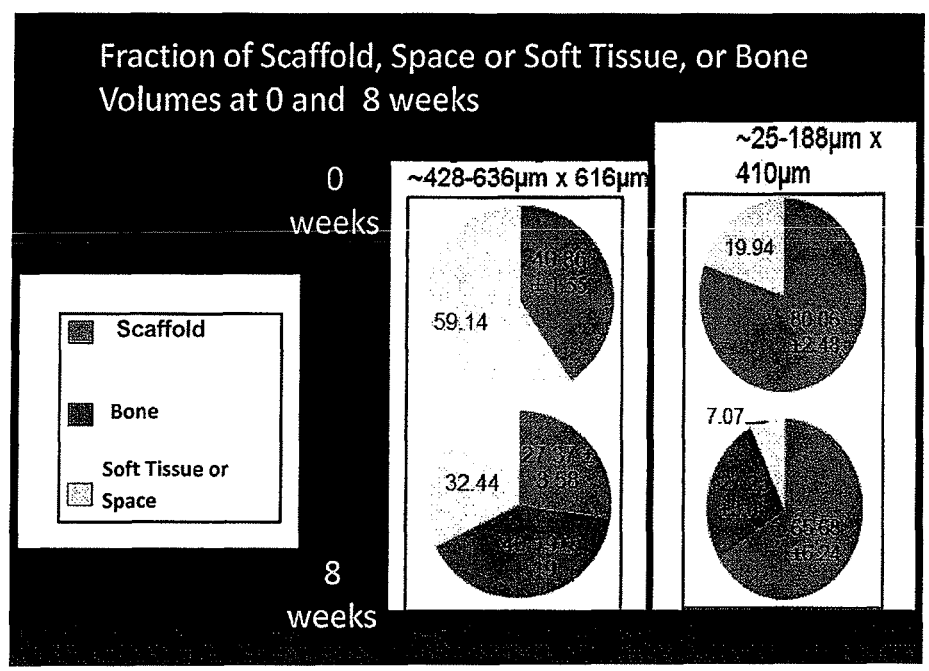
FIG. 20 graphically depicts the fraction of scaffold, space or soft tissue, and bone volumes present at 0 and 8 weeks after implant for a large pore (left) and a small pore (right) scaffold. The large pore scaffold has pore sizes in the 428-636 µm range with a z axis of 616 µm. The small pore scaffold has pore sizes in the 25-188 µm range with a z axis of 410 µm.
Figure 21:
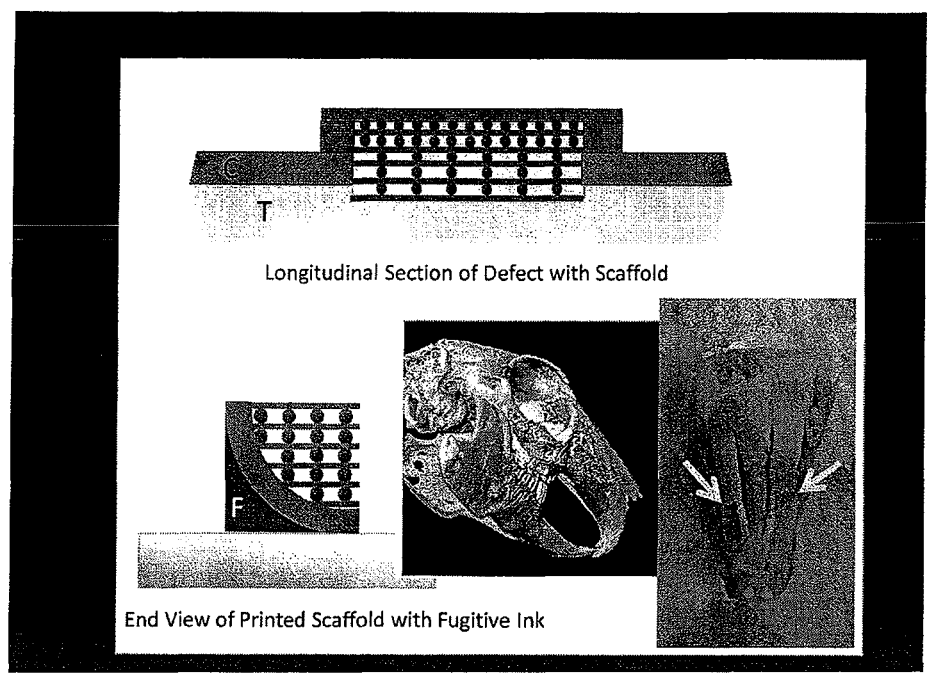
FIG. 21 provides (a) a diagram of a longitudinal section of a bone defect having a scaffold placed therein (top); (b) a diagram of a the end view of a printed scaffold (bottom left); (c) a side view of a bone defect suitable for a tissue repair device or scaffold (bottom center); and (d) a top view of a bone defect suitable for a tissue repair device or scaffold (bottom right).

Resected implants with surrounding tissue were fixed in 70% ethanol and scanned in microCT at medium resolution. Volumes of interest within each sample were the volumes occupied by each ring of unique mesopore volumes (see FIGS. 4 and 5). The outer volumetric ring of all samples was not measured because it was found that bone filled this space in an unfilled defect (Sohn et al., *J Periodontal Implant Sci* 2010; 40:180-187). Each SP scaffold contained 6 uniquely sized mesopore rings: 3 concentric ring volumes for each 1Z and 2Z location. Each LP scaffold contained 2 uniquely sized mesopore volumes, formed by the concentric rings within the 3Z locations. For each unique ring of mesopores, volume percentages for bone, scaffold, and soft tissue/space were obtained by setting two thresholds: scaffold (S) and scaffold+bone (SB). Percentage of bone ingrowth was measured by subtracting S from SB, and percentage of soft tissue/space was measured by subtracting SB from 100%. Scaffold resorption was measured by subtracting S from scaffold volumes measured before implantation. (See, FIGS. 7, 9, 10).

Figure 6:
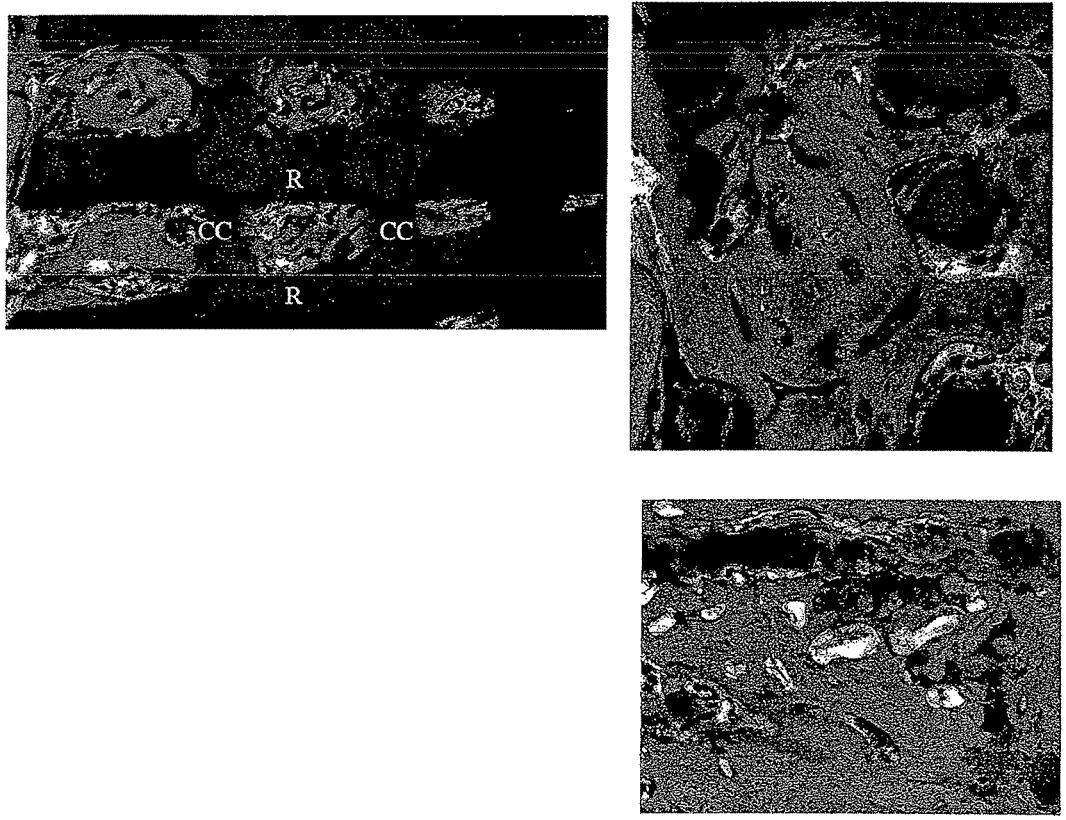
FIG. 6 shows (left) a horizontal slice from SP scaffold after 8 weeks through 1Z height mesopores, with pores formed by concentric circle (CC) and radial (R) struts. All pores but the largest on the outside were evaluated with microCT. As R struts narrowed, bone began to attach to struts. Bone appears discontinuous because it grew upward from between CC rings, as shown in image on (upper-right), a vertical slice of 1Z and 2Z height mesopores at outer ring from same scaffold. (lower-right), horizontal slice of LP scaffold after 16 weeks. Note the significant formation osteiod (green) where resorbed struts are being replaced with new bone.
Figure 8:
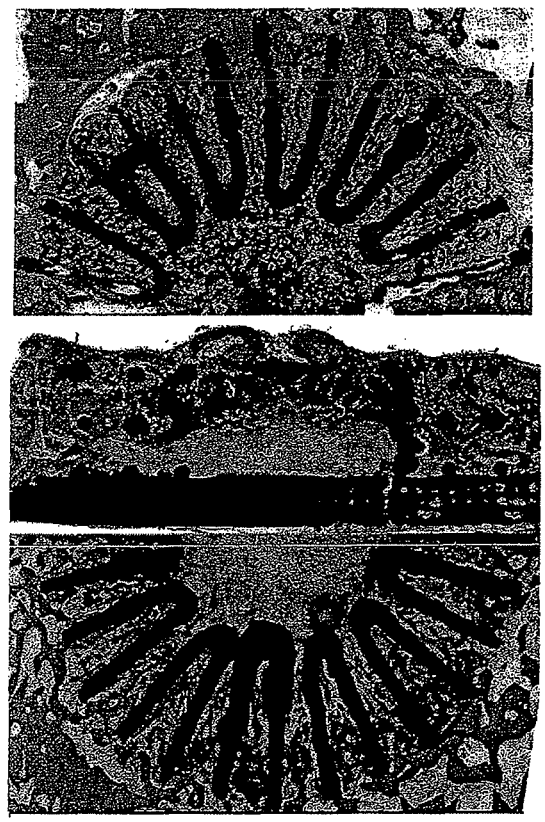
FIG. 8 provides a vertical slice through center and horizontal slices through middle of 3Z mesopores in LP scaffold after 8 weeks.

Samples were then embedded in methylmethacrylate for histology, and 80 μm thick slices were prepared at specific points through the R layers of each sample. For each SP scaffold, horizontal slices (parallel to cap) were taken through the 1Z and the two 2Z mesopore sections. For each LP scaffold, horizontal slices were taken through the two 3Z mesopores. Furthermore, a vertical slice (perpendicular to cap) was taken through the center of all scaffolds. All slices were stained and digitally photographed. (See, FIGS. 6, 8)

Other samples were examined using scanning electron microscopy (SEM) (Hitachi) with backscattered electron imaging (BEI) and EDAX evaluation to analyze mineral composition. Based on earlier studies (Simon et al., *J Blamed Mater Res* 2008; 85A:371-377), the sample size used here had statistical power to determine a 15-20% difference between groups with a p value of less than 0.05.

Results

Micro CT and histological analysis revealed bone ingrowth into mesopores of all dimensions. Higher percentages of bone were found in the larger pores at the perimeter of both SP and LP scaffolds. In general, more scaffold strut resorption occurred in areas with higher bone ingrowth. Though in the SP scaffold, at the inner ring of 2Z mesopores, which contained smaller volumes with less bone growth, strut resorption was higher. Histological results of these more closed areas showed bone which grew directly on the struts, rather than between them. In the 1Z mesopores, bone did not appear to grow inward from the perimeter, but rather grew from between CC rings from 2Z mesopores.

The CS filler appeared to resorb as bone filled in, however histology images showed remaining islands of precipitate, which SEM, BEI, and EDAX showed to be calcium phosphate (CaP). This has been reported in other studies. In most animals, the CaP appeared to conduct bone growth and integrate with bone formation, but in other animals, areas of highly dense CaP precipitation appeared to block bone formation.

Discussion

Variable mesopore scaffolds made of TCP and filled with CS allow designing scaffolds to regrow bone structure similar to cortical and trabecular bone. It is important to note that analysis of histology is still ongoing. The large accumulation of CaP precipitate is believed to be a result of a saturated solution $Ca^{2+}$ and $PO_4^{3-}$ which accumulated in the tight mesopore spaces as CaS resorbed. The acidic nature of dissolving CaS may also have increased the release of $Ca^{2+}$ and $PO_4^{3-}$ from the TCP of surrounding scaffold struts.

MicroCT results after 8 weeks show a gradient of percentages of scaffold+ bone (SB) of roughly 68-99% and a gradient of scaffold resorption of 4-14%. Most surprisingly, the mespore volumes which maximized scaffold resorption near 14% were near opposite ends of the volume spectrum, the larger being 428-636 μm×616 μm and the smaller 188-253 μm×410μ. Of these two volumes, the larger gave an SB of 67.56% (40.19% B+27.37% S) and the smaller an SB of 92.93%. (27.25% B+65.68% S), closely resembling the bone percentages of trabecular and cortical bone, respectively. Although the smaller mesopores conducted less bone, they appeared to cause equally high strut resorption because of how they directed the bone front, with associated osteoclasts, directly along the strut surfaces.

These data demonstrate the relationship between bone ingrowth/remodeling and pore volume. Future studies will test scaffold designs using pore dimensions designed to regenerate micoanatomically correct bone. Control of resorption of these scaffolds will allow their use for facial reconstruction of children with craniofacial deformities.

Example 2

Background

Repair of bone lost to trauma, disease, or birth defect currently requires regeneration of large volumes of structurally complex bone. This typically involves autogenous bone grafting, which is an imperfect process due to procurement morbidity, longer operative time, and limited bone availability. Furthermore, current alternatives to autogenous grafts each contain their own unique downsides. Processed human cadaver bone and xenogenic bone, while sparing the need for a secondary surgical site, risk transmitting infection and triggering autoimmune reactions. Additionally, treatment with alloplastic materials, such as calcium phosphate ceramics and cements, though osteoconductive and/or osteoinductive, are mechanically unstable in large defects and incapable of complete osteolastic resorption. Thus, research teams have been working to design calcium phosphate scaffolds that are both mechanically stable and resorbable.

One such scaffold material, a biphasic composite of hydroxyapatite (HA) and beta-tricalcium phosphate (β-TCP), is commonly known as biphasic calcium phosphate (BCP). The development of BCP as a bone graft material was based on the concept of the preferential dissolution of β-TCP over HA.

Bone ingrowth into BCP scaffolds mimics primary bone formation into a defect or wound site, which occurs as directional growth of new immature trabeculae, from the endosteal or periosteal layers of damaged cortical and cancelous bone into the defect. This only occurs, however, if the scaffold has appropriate surface chemistry and microtexture, for osteoconduction, and can only occur in a structurally controlled manner with the appropriately selected scaffold mesostructure (50-1000 range).

The use of solid freeform fabrication such as Direct Write (DW) fabrication allows us to print 3-D scaffolds composed of osteoconductive biomaterials that have the potential to be custom-fabricated to repair large complex defects. Complex multicomponent biphasic (COMBI) scaffolds have been produced by DW and studied in vitro. Current literature still debates optimum and threshold pore sizes required for bone ingrowth.

A COMBI scaffold has been designed which contains a graded mesopore spacing in all (X, Y, and Z) planes. The present study will test this design in vivo in a bilateral critical-sized (unable to close on its own) rabbit calvarial defect model to demonstrate how pore size affects bone density, extent of ingrowth, and bone/scaffold remodeling.

Methods

Two uniquely structured scaffolds, one with larger pore sizes and one with smaller pore sizes, were designed by overlaying, in the Z plane, layers of concentric circles with 1, 2, or 3 layers of radially oriented struts. All scaffolds were designed with a solid cap on one end to prevent soft tissue invasion and an open antrum on the other as a result of inner circular layers. Such scaffolds were fabricated by DW, printed as COMBI structures from 15:85 HAP/β-TCP, and then sintered at 1100° C. Surgical grade calcium sulfate was used as a temporary filler to prevent soft tissue invasion and/or infection through the mesopores. The outer ring of all scaffolds was removed with a dental drill to open the outer barrier created by the layering of radial strut during the printing process.

In 8 New Zealand white rabbits, one large and one small-pore scaffold were embedded bilaterally by the rabbit trephine model. In 7 rabbits, 14 scaffolds were removed after 8 weeks for analysis. The 2 scaffolds were removed from the remaining rabbit after 16 weeks for analysis. The amount of bone ingrowth and scaffold remodeling as fractions of mesopore volume were quantified by MicroCT(Scanco Medical). Samples were dehydrated with alcohol, cleared with methylsalicylate, and then embedded in polymethylmethacrylate (PMMA). Large pore scaffolds were sectioned into one central vertical slice and two horizontal slices through the 3 z height mesopores. Small pore scaffolds were sectioned in one central vertical slice, two horizontal slices through the 2 z mesopores, and one horizontal slice through the 1 z mesopore. Sections were evaluated using scanning electron microscopy (SEM; S-3500 N, Hitachi Instruments) and histology with light microscope (Aperio).

Results

Scaffold volume was designed to vary by ring section. Bone volume was higher in the more open, less scaffold-dense areas. Pores ranged from around 100 to 940 microns. Bone grew into all varied height layers, but appeared to take longer to get through largest pore sizes. Pores larger than 500 microns still filled with bone well contrary to previous literature reports. Scaffold volume was designed to vary by ring section. Bone volume was higher in the more open, less scaffold-dense areas. Pores ranged from around 100 to 940 microns. Bone grew into all varied height layers, but appeared to take longer to get through largest pore sizes. Pores larger than 500 microns still filled with bone well contrary to previous literature findings.

Table 1 relates the ratio of scaffold volume to total volume in A) 8 large pore scaffolds after printing, B) the superficial mesopores of 3 large pore scaffolds after 8 weeks, and C) the deep mesopores of 3 large pore scaffolds after 8 weeks.

| A | | | |
|---|---|---|---|
| Totoal mesopores | Outer Ring | Middle Ring | Inner Ring |
| After Printing | | | |
| Mean | 33.67 | 40.83 | 55.78 |
| SD | 1.83 | 1.55 | 0.72 |

| B | | | |
|---|---|---|---|
| Superficial mesopore | Outer Ring | Middle Ring | Inner Ring |
| After 8 Weeks | 17.07 | 24.09 | 43.47 |
| | 16.31 | 28.63 | 45.85 |
| | 9.55 | 32.16 | 55.63 |
| Mean | 14.31 | 28.29 | 48.32 |
| SD | 4.14 | 4.05 | 6.44 |

| C | | | |
|---|---|---|---|
| Deep mesopore | Outer Ring | Middle Ring | Inner Ring |
| After 8 Weeks | 11.74 | 24.13 | 38.96 |
| | 16.3 | 22.36 | 47.87 |
| | 13.82 | 31.22 | 52.13 |
| Mean | 13.95 | 25.90 | 46.32 |
| SD | 2.28 | 4.69 | 6.72 |

While the present invention has been set forth in terms of a specific embodiment or embodiments, it will be understood that the present scaffolds and methods herein disclosed may be modified or altered by those skilled in the art to other configurations. Accordingly, the invention is to be broadly construed and limited only by the scope and spirit of the claims appended hereto.

What is claimed is:

1. A tissue repair device or scaffold comprising:
   a porous bone ingrowth structure formed and shaped to customize the shape of tissue or bone repair desired to optimally span a defect so as to customize bone growth, wherein the porous bone ingrowth structure comprises interconnected struts formed by ejecting a colloidal ink from a print nozzle during a three dimensional printing process, wherein the colloidal ink consists essentially of ceramic particles in a water-based slurry comprising organic chemicals that control handling of the colloidal ink, wherein the interconnected struts comprise resorbable components to provide additional space for bone ingrowth over time, and wherein the interconnected struts define mesopores for bone ingrowth; and
   a microporous shell surrounding the porous bone ingrowth structure.

2. A tissue repair device or scaffold according to claim 1 wherein the microporous shell is extended as a guide to stabilize the tissue repair device or scaffold between one or more ends of bone.

3. The tissue repair device or scaffold according to claim 1 having a center defined by an empty space.

4. The tissue repair device or scaffold according to claim 1 wherein the porous ingrowth structure is infiltrated with a soluble filler or a soluble carrier.

5. The tissue repair device or scaffold according to claim 4 wherein the soluble filler or the soluble carrier comprises calcium sulfate.

6. The tissue repair device or scaffold according to claim 4 wherein the soluble filler or the soluble carrier comprises one or more of an antibiotic, a growth factor, a differentiation factor, a cytokine, a drug, or a combination thereof.

7. The tissue repair device or scaffold according to claim 1 wherein each of the interconnected struts has a diameter in a range from 100-350 µm.

8. The tissue repair device or scaffold according to claim 1 wherein each of the interconnected struts has a diameter in a range from 2× to substantially the same diameter as bone trabeculae.

9. The tissue repair device or scaffold according to claim 1 wherein at least two of the interconnected struts are separated longitudinally by an intervening empty space of at least 500 µm.

10. The tissue repair device or scaffold according to claim 1 being porous and comprising mesopores present in a size generally more than about 20 µm diameter.

11. The tissue repair device or scaffold according to claim 1 wherein the interconnected struts are arranged in a substantially linear arrangement.

12. The tissue repair device or scaffold according to claim 1 wherein, after about 8 weeks presence in vivo, at least about 25% of the tissue repair device or scaffold is resorbed.

13. The tissue repair device or scaffold according to claim 1 being at least about 50% porous.

14. The tissue repair device or scaffold according to claim 1 being operable to encourage and provide bone growth such that after about 8 weeks presence in vivo, at least about 25% of the tissue repair device or scaffold is replaced by bone.

15. The tissue repair device or scaffold according to claim 1 comprising micropores or nanopores having a diameter of about 0.1-1 nm.

16. The tissue repair device or scaffold according to claim 15 wherein one or more micropores or nanopores are infiltrated with solubilized collagen.

17. A method for promoting bone growth or treating bone fracture, defect or deficiency, the method comprising providing a tissue repair device or scaffold according to claim 1 in vivo to a region featuring a bone deficiency, fracture or void.

18. The tissue repair device or scaffold according to claim 1 wherein the interconnected struts comprise permanent components to provide long-term strength.

19. The tissue repair device or scaffold according to claim 1 wherein:
the tissue repair device or scaffold printed in an oil bath;
the tissue repair device of scaffold is removed from the oil bath and cured in a furnace.

20. The tissue repair device or scaffold according to claim 1 wherein the ceramic particles comprise one or more of hydroxyapatite (HA) ceramics and tricalcium phosphate ceramics (TCP).

21. The issue repair device or scaffold accordingly to claim 1 wherein:
the interconnected struts comprise layers of nested concentric circular struts and layers of radially oriented struts; and
one or more of the layers of radially oriented struts are disposed between adjacent layers of the nested circular struts.

22. The issue repair device or scaffold accordingly to claim 21 wherein nested concentric circular struts and the radially oriented struts combine to define mesopores providing a radially continuously variable porosity.

23. The issue repair device or scaffold accordingly to claim 1 wherein the three dimensional printing process is a three dimensional direct writing process.

24. A method of producing a tissue repair device or scaffold useful for promoting bone growth or treating bone fracture, defect or deficiency, the method comprising:
forming a porous bone ingrowth structure and a microporous shell that surrounds the porous bone ingrowth structure by ejecting a colloidal ink from a print nozzle during a three dimensional printing process, wherein the colloidal ink consists essentially of ceramic particles in a water-based slurry comprising organic chemicals that control handling of the colloidal ink, wherein the interconnected struts comprise resorbable components to provide additional space for bone ingrowth over time, wherein the interconnected struts define mesopores for bone ingrowth, wherein the porous bone ingrowth structure is formed and shaped to customize the shape of tissue or bone repair desired to optimally span a defect and
infiltrating the porous bone ingrowth structure with a soluble filler or soluble carrier.

25. A method according to claim 24 wherein the soluble filler or soluble carrier comprises one or more of an antibiotic, a growth factor, a differentiation factor, a cytokine, a drug, or a combination of these agents.

26. The method according to claim 24, wherein the three dimensional printing process is a three dimensional direct writing process.

* * * * *